(12) United States Patent
Kawano et al.

(10) Patent No.: US 7,330,276 B2
(45) Date of Patent: Feb. 12, 2008

(54) OPTICAL INTERFERENCE SUBSTRATE, TARGET DETECTING SUBSTRATE, TARGET DETECTING APPARATUS, AND TARGET DETECTING PROCESS

(75) Inventors: Tetsuo Kawano, Shizuoka (JP); Tomohiro Kodama, Shizuoka (JP); Shintaro Washizu, Shizuoka (JP); Takatoshi Kinoshita, Aichi (JP)

(73) Assignee: FUJIFILM Corporation, Tokyo (JP)

( * ) Notice: Subject to any disclaimer, the term of this patent is extended or adjusted under 35 U.S.C. 154(b) by 657 days.

(21) Appl. No.: 10/859,244

(22) Filed: Jun. 3, 2004

(65) Prior Publication Data
US 2004/0252301 A1   Dec. 16, 2004

(30) Foreign Application Priority Data
Jun. 12, 2003  (JP) .............................. 2003-168425

(51) Int. Cl.
*G01B 9/02*  (2006.01)
(52) U.S. Cl. ..................................................... 356/517
(58) Field of Classification Search ................ 356/503, 356/504, 517
See application file for complete search history.

(56) References Cited

U.S. PATENT DOCUMENTS

| | | | |
|---|---|---|---|
| 4,332,476 A | 6/1982 | Stenberg et al. | |
| 4,647,207 A | 3/1987 | Bjork et al. | |
| 5,289,266 A * | 2/1994 | Shih et al. ................... | 356/504 |
| 7,202,954 B2 * | 4/2007 | Washizu et al. ............. | 356/504 |
| 2003/0112446 A1 * | 6/2003 | Miller et al. ................. | 356/504 |
| 2004/0223881 A1 * | 11/2004 | Cunningham et al. ... | 422/82.05 |
| 2005/0019217 A1 * | 1/2005 | Sander et al. ............. | 422/82.05 |
| 2005/0059158 A1 * | 3/2005 | Iordanov et al. ......... | 422/82.05 |
| 2005/0196876 A1 * | 9/2005 | Chan et al. .................. | 436/518 |

FOREIGN PATENT DOCUMENTS

| | | |
|---|---|---|
| JP | 61-34442 A | 2/1986 |
| JP | 62-57936 B2 | 12/1987 |
| JP | 63-127160 | 5/1988 |

(Continued)

OTHER PUBLICATIONS

Padley, Paul, "Reflectance and Transmittance" The Connexions Project, Jul. 21, 2005 pp. 1 and 2.*

(Continued)

*Primary Examiner*—Patrick Connolly
(74) *Attorney, Agent, or Firm*—Sughrue Mion, PLLC

(57) ABSTRACT

Provided are target detection substrate for target detecting apparatuses capable of detecting various targets such as pathogens, biological substances and toxic substances without using a costly measuring apparatus; which can detect these targets with a low measurement error, high efficiency, simplicity, speed and sensitivity; and which can make a quantitative detection thereof. The target detection substrate includes at least a target interaction part which can interact with a target on an optical interference substrate, which optical interference substrate includes a substrate and a different refractive index film having a different refractive index from that of the substrate disposed on the substrate, and interferes irradiated light to radiate it as interference light where the total number of peak tops and peak bottoms in a graph of transmittance against wavelength of the interference light is from 1 to 20 in an arbitrary wavelength range of 100 nm.

32 Claims, 10 Drawing Sheets

FOREIGN PATENT DOCUMENTS

| JP | 04-78122 A | 3/1992 |
|---|---|---|
| JP | 7-32720 B2 | 4/1995 |
| JP | 10-288616 A | 10/1998 |
| JP | 2001-235473 A | 8/2001 |
| JP | 2002-116208 A | 4/2002 |
| JP | 2002-122603 A | 4/2002 |

OTHER PUBLICATIONS

Takatoshi Kinoshita, "Control of Superfine Structure of Membrane and Their Characterization", *Polymer,* Sep. 2001, pp. 648-651, vol. 50, Dept. of Engineering, Nagoya Institute of Technology.

Takeyuki Kawaguchi, et al., "A Device for Visual Detection of Antigens and Antibodies by Means of Light Interference", *Thin Solid Films,* 1990, pp. 369-381, vol. 191 (Elsevier Sequoia).

"Color Tone Control By External Stimuli, Nagoya Institute of Technology, Imitating Function of Bio-skins Applicable to Display Devices", *Nikkan Kogyo Shinbun,* Dec. 28, 2000.

Tomokio Doi, et al., "Building and control of peptide type signal transfer function", *Symposium: Building of Molecular Composition and Its Function,* A506, Nov. 28, 2000, Dept. of Engineering, Nagoya Institute of Technology, Symposium held by JST.

Hidenori Yokoi, et al., "Preparation of Amphiphilic α-helix LB film", *Polymer Preprints, Japan,* vol. 49, No. 12 IS07, Dept. of Materials Science & Engineering, Nagoya Inst. of Technology, 2000 (The society of Polymer Science, Japan).

Hidenori Yokoi, et al., "Evaluation of molecular orientation of amphiphilic α-helix water surface monomolecular film", *Polymer Preprints, Japan,* vol. 49, No. 13 lipd090, Dept. of Materials Science & Engineering, Nagoya Inst. of Technology, 2000 (The society of Polymer Science, Japan).

Yoshio Okahata, "Sensing of Odorous and Bitter Substances by using a Bilayer Molecular Film-coated Quarts Oscillator", *Biophysics,* vol. 28, No. 6 Pandect, Dept. of Polymer Chemistry, Tokyo Institute of Technology, 1988.

Yoshio Okahata, "Prospect for Chemical Information Conversion Membrane,—Molecular Recognition to be realized on a Lipid Bilayer Molecular Membrane", *SEN-I GAKKAISHI (Fiber and Industry),* vol. 46, No. 2, Feature: Functional Macromolecular Membranes Films, 1990.

Katsuhiko Ariga, et al., "Evaluation of the Viscoelasticity of the Membrane with the Use of a Quarts Oscillator,—Phase Transition of the LB film-", vol. 28 No. 11, Dept. of Biomolecular Engineering, Tokyo Institute of Technology, 1990.

Hidenori Yokoi, et al., "The Two Dimensional Orientation Control of Amphiphilic α-helix Molecule", *The 48th Symposium on Macromolecules,* II P f094, Dept. of Materials Science & Engineering, Nagoya Institute of Technology, Oct. 6, 1999, Niigata.

Hidenori Yokoi, et al., "The pH Dependence of Molecular Orientation in Monolayer Composed of Amphiphilic α-helix Molecule at Air-water Interface", *The 49th Annual Meeting of the Society of Polymer Science, Japan (SPSJ),* I p. 173, Dept. of Materials Science & Engineering, Nagoya Institute of Technology, May 29, 2000, Nagoya.

Hidenori Yokoi, et al., "Preparation of LB Film consisting of Amphiphilic α-helix Molecule", *The 49th Symposium on Macromolecules,* IS 07, Dept. of Materials Science & Engineering, Nagoya Institute of Technology, Sep. 27, 2000, Sendai.

Hidenori Yokoi, et al., "Evaluation of molecular orientation of amphiphilic α-helix water surface monomolecular film", *The 49th Symposium on Macromolecules,* IIPd090, Dept. of Materials Science & Engineering, Nagoya Institute of Technology, Sep. 27, 2000, Sendai.

Y. Nagata, et al., "Preparation and Function of Polypeptide Containing a Substrate-binding Site at the Molecular Terminal", *The 43rd Annual Meeting of the Society of Polymer Science, Japan (SPSJ),* Nov. 9, 2006, Dept. of Materials Science & Engineering, Nagoya Institute of Technology, Nagoya (Y. Nagatam et al.), and Nat'l. Institute of Materials and Chemical Research, Tsukuba (N. Minoura), May 26, 1994, Nagoya.

Hirofumi Hosokawa, et al., "Functional Control of Polypeptide Containing an Inclusion Terminal Group", *The 44th Annual Meeting of the Society of Polymer Science, Japan (SPSJ),* II Pel 119, Dept. of Materials Science & Engineering, Nagoya Institute of Technology, Nagoya (H. et al.), and Nat'l. Institute of Materials and Chemical Research, Tsukuba (N. Minoura), May 30, 1995, Yokohama.

Hirofumi Hosokawa, et al., "Functional Control of Polypeptide Containing an Inclusion Terminal Group", *Preprints of Annual meeting of the Society of Fiber Science and Technology, Japan,* G-264 3G17, Dept. of Materials Science & Engineering, Nagoya Institute of Technology, Nagoya (H. et al.), and Nat'l Institute of Materials and Chemical Research, Tsukuba (N. Minoura), Jun. 29, 1995, Tokyo (Sen-i Gakkai).

Hirofumi Hosokawa, et al. "Monolayer of polypeptide containing a cyclodextrin at the terminal", *45th Annual Meeting of Society of Polymer Science of Japan,* IIIPb100, Nagoya Institute of Technology (H. et al.) and Nat'l. Institute of Materials and Chemical Research (N. Minoura), May 29, 1996, Nagoya.

Hirofumi Hosokawa, et al., "Molecular orientation of polypeptide containing a cyclodextrin at the terminal in the monolayer and its function", *45th Symposium of Society of Polymer Science of Japan,* 2Pb44, Nagoya Institute of Technology, Oct. 2, 1996, Horoshima.

Hirofumi Hosokawa, et al., "Structural control of polypeptide containing an active site at the terminal in monolayer and its function", *46th Annual Meeting of Society of Polymer Science of Japan,* IIPb108, Nagoya Institute of Technology, May 24, 1997, Tokyo.

Atsushi Kato, et al., "Characterization of polypeptide monolayer containing the molecular recognition site", *47th Annual Meeting of Society of Polymer Science of Japan,* IIIPd124, Nagoya Institute of Technology, May 29, 1998, Kyoto.

Atsushi Kato, et al., "Characterization of polypeptide monolayer containing a cyclodextrin at the terminal", *29th Annual Meeting of Union of Chemistry-Related Societies in Chubu Area, Japan,* IB0705, Faculty of Engineering, Nagoya Institute of Technology, Oct. 3, 1998, Toyohashi.

Hidenori Yokoi, et al., "The control of molecular orientation in monolayer of amphiphilic α-helix", *Preprints presented at 15Symposium of Membrane Science and Technology,* 3PA53, Faculty of Engineering, Nagoya Institute of Technology; Core Research for Evolutional Science and Technology (CREST), May 12, 1999, Chiba (Seni-Gakkai).

Tomokiyo Doi, et al., "The molecular orientation and oscillation of polypeptide monolayer at oil/water interface", *48th Symposium of Society of Polymer Science of Japan,* IIIJ02, Faculty of Engineering, Nagoya Institute of Technology; Core Research for Evolutional Science and Technology (CREST), Oct. 8, 1999, Niigata.

Tomokiyo Doi, et al., "Creation of peptide-type signal transmitting function and control of its function" *Open Symposium of Creation and Functions of New Molecules and Molecular Assemblies sponsored by Core Research for Evolutional Science and Technology (CREST),* A506, Faculty of Engineering, Nagoya Institute of Technology, Nov. 28, 2000, at Japan Science and Technology Corporation (JST), Tokyo.

"Molecular alignment of poly (γ-methyl-L-glutamate) containing a β-cyclodextrin at the terminal and molecular indentification (n-hexane/water interface)", *Control of molecular alignment of polypeptide molecular film,* published by Dr. Tomokio Doi, chapter 4, 2000.

Tomokiyo Doi, et al., "The Control of Structure and Functions of LB-Film Composed of Bio-Related Polymers", *First International Symposium on Biomimetic Materials Processing,* Jan. 11, 2001, p. 19, Nagoya.

Takatoshi Kinoshita, "Preparation of a Structural Color Forming System by Polypeptide-Based LB Films", *The fourth NIMC International Symposium on Photoreaction Control and Photofunctional Materials,* Mar. 14, 2001, pp. 1-9-1-12, Ibaragi.

Hidenori Yokoi, et al., "Nano-Phase Separation in the Monolayer Composed of α-Helical Copolypeptide at Air/Water Interface", *Chemistry Letters 2000*, pp. 1210-1211 (The Chemical Society of Japan).

Y. Mouri, et al., "Molecular Recognition and Polypeptide Orientation in the Monolayer at Oil/Water Interface", *12th Academic Symposium of MRS-Japan manuscripts*, Dec. 7, 2000, p. 66, Kanagawa.

Hirofumi Hosokawa, et al., "The Molecular Orientation of a Peptide-based Amphiphile at Hexane/Water Interface", *Chemistry Letters 1997*, pp. 745-746, The Chemical Society of Japan.

T. Kinoshita, et al., "The guest-induced oscillation of a monolayer composed of polypeptide containing β-cyclodextrin at the terminal", *Chaos*, vol. 9 No. 2, 1999, pp. 276-282, American Institute of Physics.

T. Kinoshita, et al., "Structural color forming system composed of polypeptide-based LB films", *Nanotechnology and Nano-Interface Controlled Electronic Devices*, pp. 233-252, 2003, Elsevier Science.

T. Miyagi, et al., "Structural Color with Polypeptide LB Film", *Transactions of the Materials Research Society of Japan 27* [3], pp. 555-558, 2002.

H. Yokoi, et al., "Polypeptide membranes at an interface" *Prog. Polym. Sci.*, pp. 341-357, 2003.

A. Brecht et al., "Direct Monitoring of Antigen-Antibody Interactions by Spectral Interferometry," Sensors and Actuators B, vol. 6, 1992, pp. 96-100.

* cited by examiner

OPTICAL INTERFERENCE SUBSTRATE, TARGET DETECTING SUBSTRATE, TARGET DETECTING APPARATUS, AND TARGET DETECTING PROCESS

BACKGROUND OF THE INVENTION

1. Field of the Invention

The present invention relates to target detecting apparatuses and target detecting processes which can detect various targets such as pathogens, biological substances and toxic substances without using a costly measuring apparatus, which can detect these targets with a low measurement error, high efficiency, simplicity, speed and sensitivity, and which can make a quantitative detection thereof. The present invention also relates to target detection substrates and optical interference substrates which can suitably be used in such apparatuses and processes.

2. Description of the Related Art

In the related art, various kinds of processes have been considered for detecting targets such as pathogens, biological substances and toxic substances, for example, enzyme immunoassay methods such as ELISA. However, in these processes, there was the problem of having to use expensive fluorescent labels or dangerous radiation markers.

Recently, apparatuses and processes have been proposed which detect targets by detecting an interference color change of interference light by a detection layer without using a fluorescence label or a radiation marker. For example, an apparatus has been proposed which measures a thickness change of a nonspecific protein layer as an interference color change using an ellipsometer or the like (e.g., JP-A No. 2002-122603 and JP-A No. 2002-116208). In other proposals, a thickness change is detected as an interference color change in a light reflecting surface by a nucleic acid chain (e.g., Japanese Patent Application Publication (JP-B) No. 07-32720, JP-A No. 10-288616 and JP-A No. 2001-235473). Apparatuses have been proposed wherein light emitted from a light source is irradiated onto a sample surface via a polarizer, the reflected light is reflected by a polarization modulator, and then detected via a polarizer (e.g., JP-A No. 61-34442, JP-A No. 04-78122, JP-B No. 62-57936 and U.S. Pat. No. 4,332,476). Moreover, an apparatus has been proposed which measures a thickness change of a nonspecific protein layer as an interference color change using an ellipsometer or the like, and detects this interference light via a polarizer (e.g., JP-A No. 2002-122603).

However, in these proposals, specific wavelength peaks are measured using an interference filter, a multi-layered structure of optical interference substrates made of silicon nitride, silica, titania, or the like. These proposals therefore have low manufacturing efficiency and high cost. In addition, simple and quick measurement cannot be performed, and there are problems in that the apparatus easily picks up measurement noise, the measurement error is large, measurement sensitivity is poor and a quantitative measurement cannot be made. Thus, there are currently no target detecting apparatuses and target detecting processes which can detect various targets such as pathogens, biological substances and toxic substances without using a costly measuring apparatus, which can detect these targets with a low measurement error, high efficiency, simplicity, speed and sensitivity, and which can make a quantitative detection thereof. Also, there are no target detection substrates and optical interference substrates which can suitably be used in such apparatuses and processes.

OBJECTS AND ADVANTAGES

An object of the present invention is to provide target detecting apparatuses and target detecting processes which can detect various targets such as pathogens, biological substances and toxic substances without using a costly measuring apparatus, which can detect these targets with a low measurement error, high efficiency, simplicity, speed and sensitivity, and which can make a quantitative detection thereof. Further object of the present invention is to provide target detection substrates and optical interference substrates which can suitably be used in such apparatuses and processes.

SUMMARY OF THE INVENTION

An According to an aspect of the present invention, there is provided an optical interference substrate including a substrate and a different refractive index film disposed on or above the substrate and having a different refractive index from that of the substrate. The optical interference substrate interferes irradiated light to radiate it as interference light where the total number of peak tops and peak bottoms in a graph of transmittance against wavelength of the interference light is from 1 to 20 in an arbitrary wavelength range of 100 nm.

The difference between transmittance of a peak top and that of an adjacent peak bottom in a graph of transmittance against wavelength of the interference light within a wavelength range of from 300 nm to 800 nm may be 40% or less.

The difference of transmittance of a peak top and that of an adjacent peak bottom in a graph of transmittance against wavelength of the interference light within a wavelength range of from 300 nm to 800 nm may be 35% or less.

The different refractive index film may contain an oxygen-containing compound.

The oxygen-containing compound may be a metal oxide or a non-metal oxide.

The metal oxide may be $Ta_2O_5$, $TiO_2$, and $SiO_2$.

The thickness of the different refractive index film may be between 0.01 µm and 100 µm.

The density of the different refractive index film may be between 1.0 g/cm$^3$ and 3.0 g/cm$^3$.

The substrate may be formed of a semiconductor, ceramic, metal, glass, silica glass, or plastic.

According to another aspect of the present invention, there is provided a target detection substrate including an optical interference substrate and a target interaction part deposited on or above the optical interference substrate, in which the target interaction part is capable of interacting with a target.

The target detection substrate may be capable of radiating irradiated light as interference light, and the target interaction part may be capable of interacting with the target. The target detection substrate may be used for detecting the target by detecting a wavelength change of the interference light caused by interaction of the target interaction part with the target and a wavelength changer.

The interaction may be physical adsorption or chemical adsorption.

The target interaction part may be provided in a film-like material on the optical interference substrate.

The film-like material may be formed of at least one rod-shaped material.

The film-like material may be formed by coating, Langmuir-Brodgett method (LB method), self-assembly, and graft copolymerization.

One or more films may be further provided on the surface of the film-like material.

The film may have a refractive index substantially equal to the refractive index of the surface of the optical interference substrate adjacent to the film-like material.

The thickness of the film-like material may be between 50 nm and 1 μm.

The film-like material may be a monomolecular film of rod-shaped materials or a laminated film of the monomolecular films.

The rod-shaped material may be a rod-shaped organic molecule.

The rod-shaped organic molecule may be a spiral molecule.

The spiral molecule may be an α-helix polypeptide.

The target interaction part may be a target acceptor capable of capturing a target.

The wavelength changer may include a target capturing body capable of capturing a target, and a wavelength changing material having a refractive index different from the refractive index of the different refractive index film of the target detection substrate.

The absolute value of the difference between the refractive index (n) of the different refractive index film and the magnitude of the complex refractive index of the wavelength changing material is 0.5 or more, where the refractive index (n) is represented in the formula for calculating the complex refractive index of the different refractive index film: complex refractive index=$n-ik$ (where "n" is refractive index, "k" is extinction coefficient, and "i" is imaginary number), and the magnitude of the complex refractive index is represented by the formula: magnitude of complex refractive index=$(n^2+k^2)^{0.5}$ (where "n" is refractive index and "k" is extinction coefficient).

The wavelength changing material may be a substance whose light absorbance has wavelength dependency.

The wavelength changing material may be a metal compound or a metal nanoparticle.

The metal compound may be a metal complex or a chelate compound.

The metal compound may be alkanethiol gold, benzenethiol gold, phenol gold, alkanedithiocarbonate gold, triazole gold, dialkyldithiocarbamic acid gold, aliphatic carboxylic acid gold, aromatic carboxylic acid gold, or derivatives thereof.

The metal nanoparticle may be a gold particle, platinum particle, palladium particle, zinc particle, silver particle, or nickel particle.

The target acceptor or the target capturing body may be an enzyme, coenzyme, enzyme substrate, enzyme inhibitor, host compound, metals, antibody, antigen, microorganism, parasite, bacterium, virus, virus particle, cell, cell fragment, metabolite, nucleic acid, hormone, hormone receptor, lectin, sugar, physiologically active material, physiologically active material receptor, allergen, protein, blood protein, tissue protein, nucleic substance, neurotransmitter, hapten, drug, environmental material, chemical substance, or derivatives thereof.

The host compound may be a monomolecular host compound, polymolecular host compound, polymer host compounds, or inorganic host compounds. The monomolecular host compound may be cyclodextrin, a crown compound, cyclophane, azacyclophane, calixarene, cyclotriveratrylene, spherand, cavitand, or oligopeptides. The polymolecular host compound may be urea, thiourea, deoxycholic acid, perhydrotriphenylene, or tri-o-thymotide. The polymer host compounds may be cellulose, starch, chitin, chitosan, or polyvinyl alcohol. The inorganic host compound may be an intercalation compound, zeolite, or Hofmann type complex.

The target may be avidin, and the target acceptor or the target capturing body may be biotin.

According to another aspect of the present invention, there is provided a target detection apparatus, including an optical irradiation unit which irradiates light; an optical interference unit capable of interacting with a target and a wavelength changer to thereby change the wavelength of interference light of the light irradiated by the optical irradiation unit; and a wavelength change detection unit provided in the path of the interference light. The wavelength change detection unit is capable of detecting a wavelength change of the interference light radiated by the optical interference unit, and the target interaction part of the target detection substrate is capable of interacting with the target.

The optical irradiation unit may be capable of irradiating a linear luminous flux.

The optical irradiation unit may be a laser light irradiation device.

The wavelength change detection unit may be capable of transmitting light of a specific wavelength, and of detecting transmittance of the light of the specific wavelength.

The wavelength change detection unit may include an interference filter and an optical detection sensor capable of detecting light transmitted through the interference filter.

The wavelength change detecting unit may measure spectra before and after a wavelength change of the interference light, and their differential spectrum.

The wavelength change detection unit may be capable of transforming the differential spectrum into spectral intensity, and of amplifying the spectral intensity.

The wavelength change detection unit may be a spectrophotometer.

According to another aspect of the present invention, there is provided a process for detecting a target including irradiating light to a target detection substrate; allowing the target interaction part of the target detection substrate, the target, and the wavelength changer to interact; radiating the irradiated light as interference light; and detecting a wavelength change of the interference light.

DESCRIPTION OF THE PREFERRED EMBODIMENTS

Target Detecting Apparatus

Figure 1:
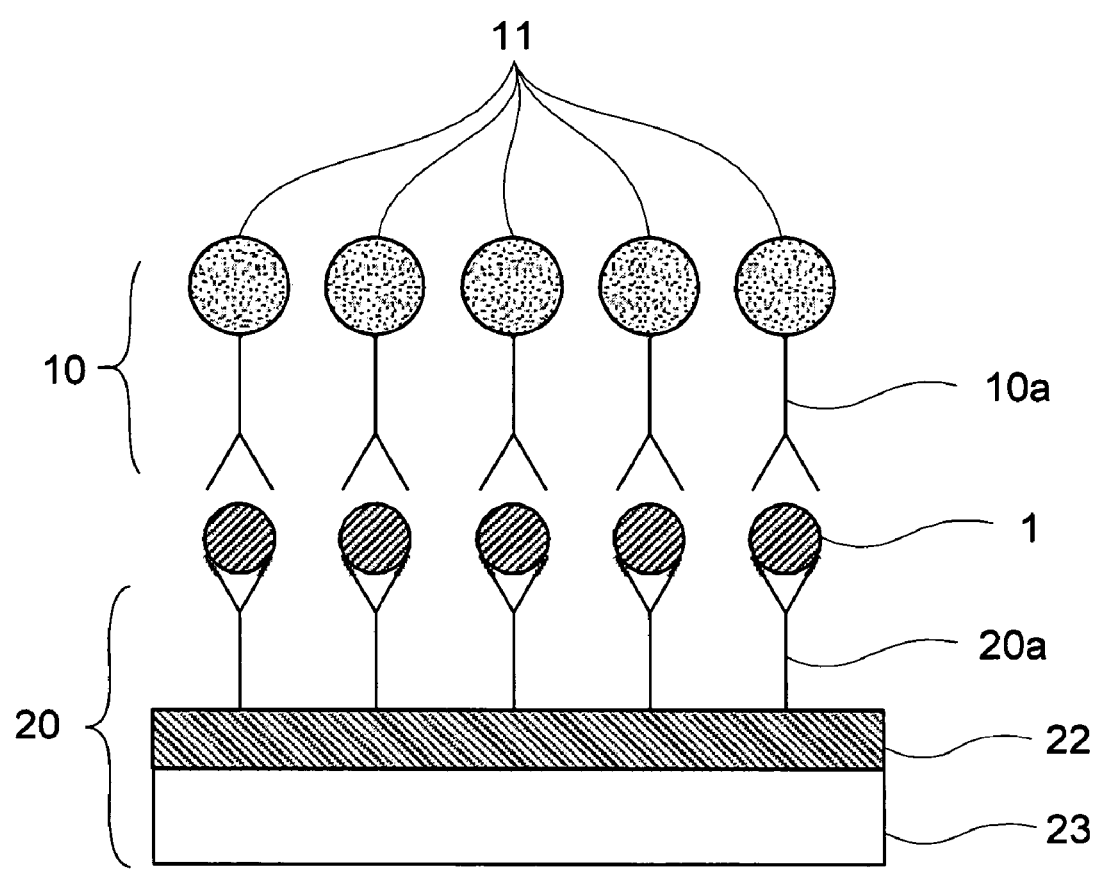
FIG. 1 is a schematic diagram showing one example of interaction of an optical interference unit (target detection substrate) according to the present invention, targets, and wavelength changers.

The target detecting apparatus of the present invention comprises an optical irradiation unit, an optical interference unit, a wavelength change detecting unit and other unit which may be suitably selected as necessary.

Optical Irradiation Unit

The optical irradiation unit is not particularly limited provided that it irradiates light, and may be selected according to the purpose from light sources known in the art such as for example a halogen lamp (e.g., xenon lamp) or a laser light irradiation device.

Among these, a laser light irradiation device is preferred as it can irradiate a linear luminous flux. In this case, it is easy to control the incidence angle of the light irradiated from this optical irradiation unit to the optical interference unit. Other advantages are that the area of the light-receiving surface in the optical interference unit irradiated by light from the optical irradiation unit can be designed small; that the light-receiving surface of the wavelength change detecting unit which detects the wavelength change of the interference light due to the optical interference unit, can be designed small; that measurement noise can be controlled; and that measurement errors can be reduced.

In the present invention, when a spectrophotometer is used as the wavelength change detecting unit, a light source built into this spectrophotometer can be used as the optical irradiation unit.

Optical Interference Unit

The optical interference unit can change the wavelength of interference light of the light irradiated by the optical light irradiation unit through interaction with targets and wavelength changers. The optical interference unit includes a target detection substrate of the present invention and may further include other members if necessary. The target detection substrate includes, on the optical interference substrate of the present invention, a target interaction part capable of interacting at least with the targets.

Optical Interference Substrate

The optical interference substrate according to the present invention includes a substrate and a different refractive index film having a different refractive index from that of the substrate disposed on the substrate, and interferes irradiated light to radiate it as interference light where the total number of peak tops and peak bottoms in a graph of transmittance against wavelength of the interference light is from 1 to 20 in an arbitrary wavelength range of 100 nm.

The optical interference substrate is not particularly limited and may be selected suitably according to the purpose provided that the total number of peak tops and peak bottoms in a graph of transmittance against wavelength of the interference light is from 1 to 20 in an arbitrary wavelength range of 100 nm. However, the total number is preferably from 1 to 15, and more preferably from 1 to 10.

When the total number of peak tops and peak bottoms exceeds 20 in an arbitrary wavelength range of 100 nm, the change of spectrum (peak shift) due to the detection reaction (interaction) may become indistinguishable, and therefore is not preferable.

Preferably, in the optical interference substrate, the difference of transmittance of a peak top and that of an adjacent peak bottom in a graph of transmittance against wavelength of the interference light within a wavelength range of from 300 nm to 800 nm is 40% or less, more preferably 35% or less, and particularly preferably 30% or less.

When the difference of transmittances is 40% or less, ripples can be observed in a graph of transmittance against wavelength where the differences of peak tops and peak bottoms are substantially constant. To form a peak as a main wavelength where the difference of transmittances of a peak top and that of an adjacent peak bottom exceeds 40%, it generally requires an interference filter having a substrate and multiple layers with different refractive indices provided thereon. Whereas interference filters are low in manufacturing efficiency and high in cost, the optical interference substrate according to the present invention can be manufactured efficiently at low cost and is advantageous in that it includes at least one layer of a different refractive index film on the surface of the substrate. Moreover, by applying the optical interference substrate to a target detection substrate and a target detection apparatus, the target detection substrate and the target detection apparatus will in turn become advantageous in that they can be manufactured efficiently at low cost.

The substrate is not particularly limited and may suitably be selected according to the purpose provided that a different refractive index film can be deposited on the surface. Suitable examples of the substrate include articles formed from semiconductors, ceramics, metal, glass, silica glass, plastics, and the like.

The shape of the substrate is not particularly limited and may be suitably selected according to the purpose, but a tabular shape is preferable.

The different refractive index film is not particularly limited and may be suitably selected according to the purpose provided that it has a refractive index different from that of the substrate. Examples include a film containing an oxygen-containing compound.

The oxygen-containing compound is not particularly limited and can be suitably selected from among oxygen-containing compounds known in the art. Examples include metal oxides, non-metal oxides, and the like.

The metal oxide is not particularly limited and can be suitably selected from among metal oxides known in the art. Examples include $Ta_2O_5$, $TiO_2$, $SiO_2$, and the like.

The non-metal oxide is not particularly limited and may be suitably selected from among non-metal oxides known in the art.

The thickness of the different refractive index film (physical film thickness) is not particularly limited, and may be suitably selected according to the purpose. However, it is preferably 0.01 μm to 100 μm, and more preferably 0.01 μm to 10 μm, and particularly preferably 0.01 μm to 5.0 μm. When the thickness is less than 0.01 μm, the ripples may not appear, and when it is more than 100 μm, too many ripples may be formed, both of which cases are not preferable.

The density of the different refractive index film is not particularly limited and may be suitably selected according to the purpose. However, it is preferably from 1.0 $g/cm^3$ to 3.0 $g/cm^3$, more preferably from 1.2 $g/cm^3$ to 2.6 $g/cm^3$, and particularly preferably from 1.4 $g/cm^3$ to 2.6 $g/cm^3$. When the density is less than 1.0 $g/cm^3$, the different refractive index film will become brittle, leading to inferior resistance of the optical interference substrate. When the density is more than 3.0 $g/cm^3$, the number of occurring ripples may be inappropriate. Therefore, both cases are not preferable.

The process for providing a different refractive index film on the surface of the substrate is not particularly limited and may be provided according to a film-forming technique known in the art. Suitable examples include EB (electron beam) vapor deposition, ion assisted deposition, ion plating, and the like.

The optical interference substrate according to the present invention has a different refractive index film provided on a substrate so that it interferes irradiated light to radiate it as interference light even if the different refractive index film is formed of one layer; forms ripples in a graph of transmittance against wavelength of the interference light; may be suitably used in various target detection substrates, target detection apparatuses, and the like based on wavelength change using ripples; and, in particular, may be suitably used in target detection substrates, target detection apparatuses, and target detection processes according to the present invention described below.

Target Interaction Part

The target interaction part is not particularly limited provided that it can interact with the target, and may be suitably selected according to the purpose, but it is preferred that it can interact with the target by at least one of physical adsorption and chemical adsorption. More preferably, the target interaction part is a target acceptor which can capture the target.

Figure 2:
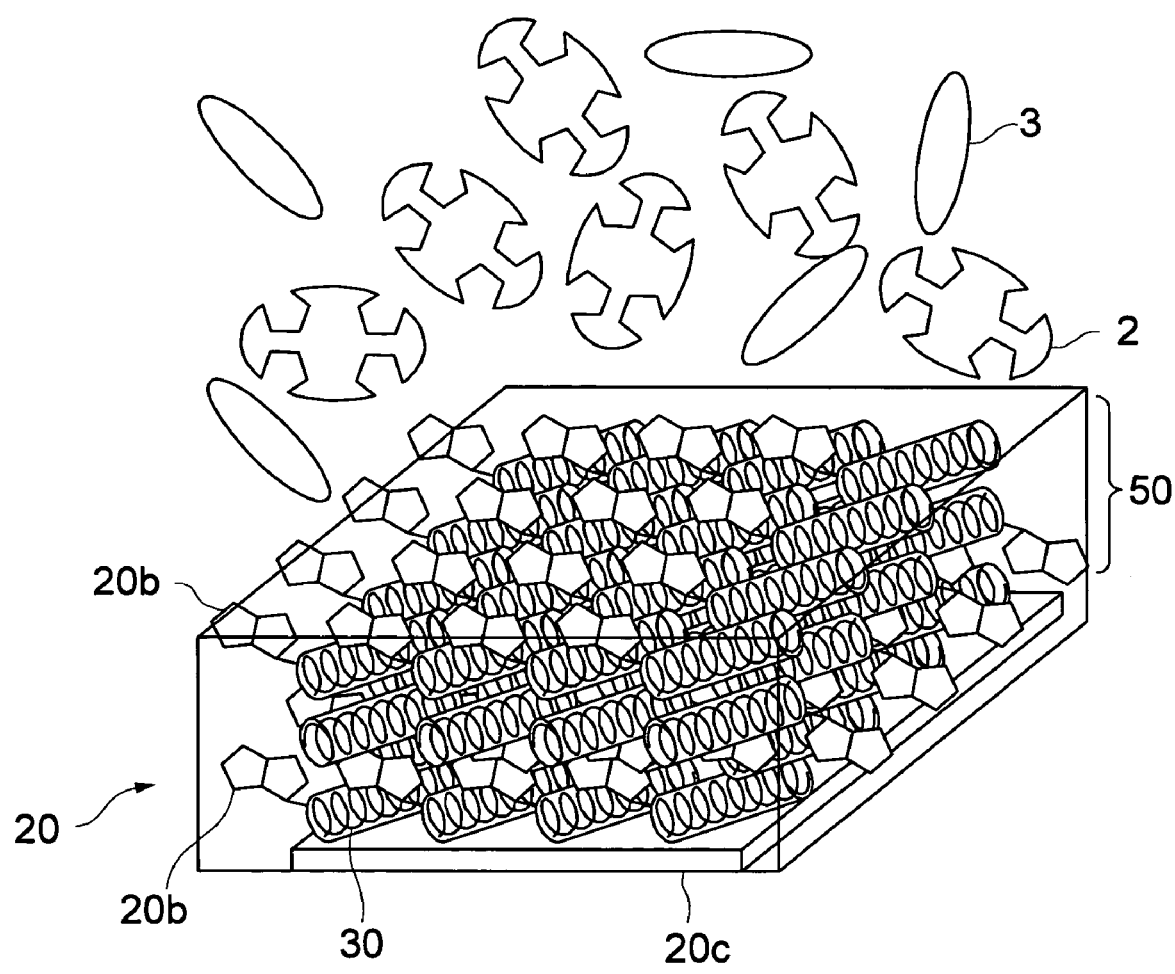
FIG. 2 is a schematic diagram showing an example of target acceptors provided in film-like material on an optical interference substrate in an optical interference unit (target detection substrate) according to the present invention.

The position where the target interaction part is provided is not particularly limited. For example, as shown in FIG. 1, a target acceptor 20a as the target interaction part may be directly provided on a different refractive index film 22, or, as shown in FIG. 2, may be provided in a film-like material 50 on an optical interference substrate 20c.

The process by which the target acceptor is directly provided on the optical interference substrate is not particularly limited and any process known in the art may be used. Examples include a process in which the optical interference substrate is immersed in a buffer solution containing the target acceptor so that the target acceptor is supported by the substrate.

Film-like Material

In case where the target interaction part is provided on the optical interference substrate via the film-like material, the film-like material is not particularly limited and may be suitably selected according to the purpose, for example it may be formed from the rod-shaped material.

The thickness of the film-like material may be suitably selected according to the wavelength of the interference light before and after wavelength change, the refractive index of the substrate, etc., but for example, it is preferably 50 nm to 1 μm.

In the present invention, one or more films may be further provided on the surface of the film-like material. This film is not particularly limited and may be selected according to the purpose, but it is preferred that the film has a refractive index which is substantially equivalent to the refractive index of the substrate surface in contact with the film-like material. In this case, interference light having a sharp spectral curve can be radiated, and even if the wavelength change (wavelength shift) of this interference light is very small, it can be detected simply, reliably, rapidly and with high sensitivity.

The film is not particularly limited and a suitably selected film may be used, but a dielectric film may for example be mentioned. The dielectric film may be formed on the surface of the film-like material according to, for example, a known process. Specifically, gold, silver, platinum, platinum/palladium, or the like may be selected as materials for the dielectric film, and a thin layer of these materials may be formed by ion coater or the like on the surface of the film-like material. The material of the dielectric is not limited to the above, and may also be an oxide such as silicon oxide.

In an aspect where the target detection substrate comprises the dielectric film on the surface of the film-like material, the whole optical interference unit or whole target detection substrate functions as the interference filter. In this case, it is advantageous in that it can be manufactured efficiently at low cost, as opposed to general interference filters.

In addition to the target detecting apparatus or the target detection process of the present invention, this target detection substrate may also be used in fields such as colorimeter, flame photometer, monochromator, laser, optical communications and optical recording.

Rod-shaped Material

The rod material is not particularly limited and can be suitably selected according to the purpose, for example a rod-shaped inorganic molecule or a rod-shaped organic molecule.

One of these may be used alone, or two or more may be used together. Among these, a rod-shaped organic molecule is preferred from the viewpoints that it easily interacts with the target, molecular treatment is easy, formation of the film-like material is easy, and even if the surface quality of the undersurface of the film-like material is not smooth, the surface on the opposite side can easily be maintained smooth.

The rod-shaped organic molecule is not particularly limited and can be suitably selected according to the purpose, e.g., a biopolymer or a polysaccharide.

Examples of the biopolymer include a fibrous protein, an α-helix polypeptide, and a nucleic acid (DNA, RNA). Examples of this fibrous protein include those having an α-helix structure such as α-keratin, myosin, epidermin, fibrinogen, tropomycin and silk fibroin.

The polysaccharide may for example be amylose or the like.

From the viewpoint of stably maintaining the rod-shape of the organic molecule, a helical molecule wherein the molecule has a helical structure is preferred. In this case, even if the surface quality (e.g., the surface quality of the optical interference substrate) of the undersurface of the film-like material is not smooth, the surface (upper surface) (surface on which light is incident from the optical irradiation unit) on the opposite side can easily be maintained smooth, and measurement errors of wavelength variation produced when the surface is not smooth, can be reduced.

Among those mentioned above, the spiral molecule may be an α-helix polypeptide, DNA, amylose, etc.

α-helix Polypeptide

The α-helix polypeptide is one of the secondary structures of a polypeptide. It is rotated once (forms one spiral) every 3.6 amino acid residues, forms substantially parallel hydrogen bonds with the spiral axis between the imido group (—NH—) and carbonyl group (—CO—) every fourth amino acid, and has a structure which is stable energywise due to the repetition of 7 amino acids as one unit.

The direction of the helix of the α-helix polypeptide is not particularly limited, and may be right-handed or left-handed. Due to stability factors, only α-helix polypeptides having a right-handed helix are found in nature.

The amino acid which forms the α-helix polypeptide is not particularly limited and may be selected according to the purpose if it can form an α-helix structure. Amino acids which can easily form this α-helix structure are preferred, examples of such amino acids being aspartic acid (Asp), glutamic acid (Glu), arginine (Arg), lysine (Lys), histidine (His), asparagine (Asn), glutamine (Gln), serine (Ser), threonine (Thr), alanine (Ala), valine (Val), leucine (Leu), isoleucine (Ile), cysteine (Cys), methionine (Met), thyrosin (Tyr), phenylalanine (Phe) and tryptophan (Trp). One of these may be used alone, or two or more may be used together.

By suitably selecting the amino acid, the α-helix polypeptide can be designed to have hydrophilicity, hydrophobicity or amphiphilicity. If hydrophilicity is conferred, the amino acid may for example be serine (Ser), threonine (Thr), aspartic acid (Asp), glutamic acid (Glu), arginine (Arg), lysine (Lys), asparagine (Asn) or glutamine (Gln). If hydrophibicity is to be conferred, the amino acid may for example be phenylalanine (Phe), tryptophan (Trp), isoleucine (Ile), thyrosin (Tyr), methionine (Met), leucine (Leu) or valine (Val).

The amino acid forming the α-helix polypeptide is not particularly limited, and may for example be a L-amino acid or D-amino acid, or a derivative thereof wherein the side chains are modified.

In the α-helix polypeptide, by esterifying the carboxyl group in the amino acid which forms this α-helix which does not form a peptide linkage, hydrophobicity can be conferred. Moreover, hydrophilicity can be conferred by hydrolyzing this esterified carboxyl group.

The number of linkages (polymerization degree) of the amino acid in the α-helix polypeptide is not particularly limited and can be suitably selected according to the purpose, but it is preferably 10 to 5000.

If the number of linkages (polymerization degree) is less than 10, the polyamino acid may not be able to form a stable α-helix, and if the number of linkages (polymerization degree) is more than 5000, it may become difficult to orient it in a perpendicular direction.

Examples of the α-helix polypeptide are polyglutamic acid derivatives such as poly(γ-methyl-L-glutamate), poly (γ-ethyl-L-glutamate), poly(γ-benzyl-L-glutamate), poly(L-glutamine acid-γ-benzyl) and poly (n-hexyl-L-glutamate); polyaspartic acid derivatives such as poly(β-benzyl-L-aspartate); poly(L-leucine); poly(L-alanine); poly(L-methionine); poly(L-phenylalanine); and poly(L-lysine)-poly(γ-methyl-L-glutamate).

The α-helix polypeptide may be suitably synthesized or prepared by a process known in the art, or a commercial product may be used.

As an example of the synthesis of the α-helix polypeptide, the block copolypeptide [poly(L-lysine)$_{25}$-poly(γ-methyl-L-glutamate)$_{60}$] PLLZ$_{25}$-PMLG$_{60}$ may be synthesized as follows. The block copolypeptide [poly (L-lysine)$_{25}$-poly(γ-methyl-L-glutamate)$_{60}$] PLLZ$_{25}$—PMLG$_{60}$, is synthesized by polymerizing N$^\epsilon$-carbobenzoxy L-lysine N$^\alpha$-carboxylic acid anhydride (LLZ-NCA) using n-hexylamine as initiator, and then polymerizing γ-methyl L-glutamate N-carboxylic acid anhydride (MLG-NCA) as shown by the following formula:

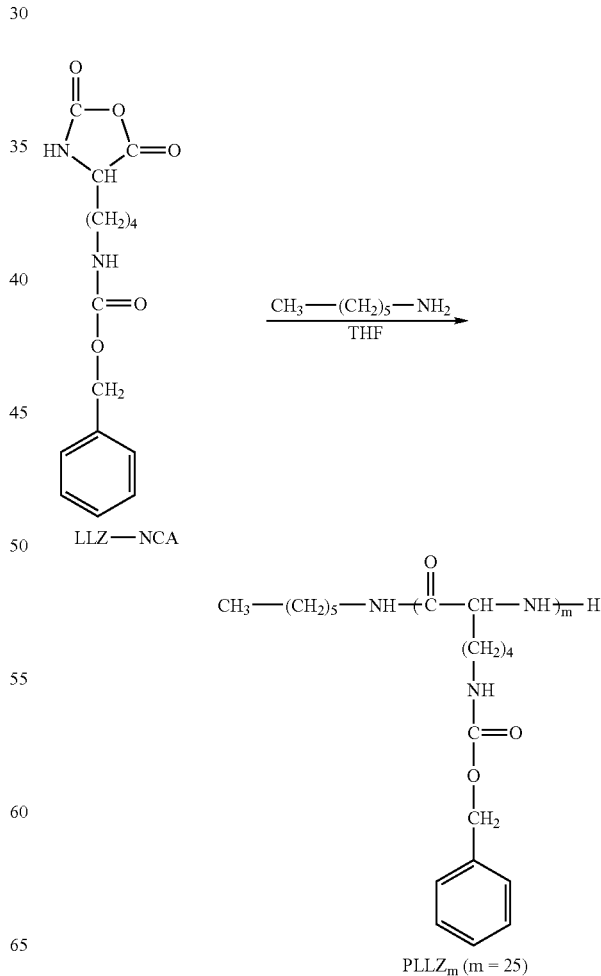

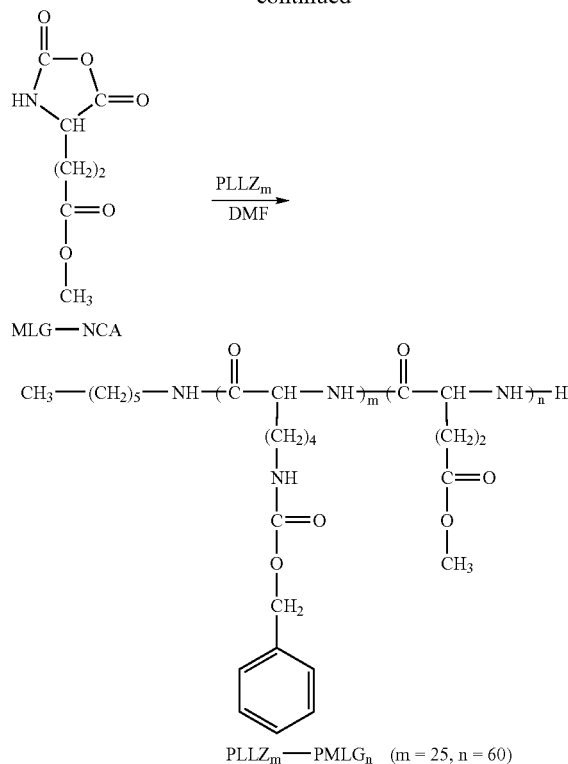

The synthesis of the α-helix polypeptide is not limited to the above, and can also be achieved by genetic engineering. For example, a host cell is transformed by an expression vector incorporating DNA which codes for the polypeptide, and this transformant is then cultured.

Examples of this expression vector are a plasmid vector, a phage vector, or the chimera vector of a plasmid and phage.

Examples of the host cell are prokaryon microorganisms such as *Escherichia coli* and *Bacillus subtilis*, eukaryon microorganisms such as yeast fungus, and animal cells.

The α-helix polypeptide may also be prepared by cutting out the α-helix structure portion from natural fibrous proteins such as α-keratin, myosin, epidermin, fibrinogen, tropomycin and silk fibroin.

DNA

The DNA may be single-stranded DNA, but from the viewpoint of stabilizing the rod shape, it is preferred that it is double-stranded DNA.

The double-stranded DNA has a double helix structure wherein two right-handed helical polynucleotide chains are positioned so that they extend in mutually opposite directions around one central axis.

The polynucleotide chain is formed by four kinds of nucleic acid bases, i.e., adenine (A), thymine (T), guanine (G) and cytosine (C). In the polynucleotide chain, the nucleic acid bases mutually project inside a plane perpendicular to the central axis, forming the so-called Watson-Crick base pairs wherein thymine is specifically hydrogen-bonded to adenine, and cytosine is specifically hydrogen-bonded to guanine, respectively. As a result, in the double-stranded DNA, two polypeptide chains are joined together complementarily.

The DNA can be prepared by the PCR (Polymerase Chain Reaction) method, the LCR (Ligase Chain Reaction) method, the 3SR (Self-sustained Sequence Replication) method, the SDA (Strand Displacement Amplification) method, and other methods known in the art, but among these, the PCR method is preferred.

The DNA may be directly cut out enzymatically with a restriction enzyme from a natural gene, prepared by a gene cloning method, or prepared by a chemosynthesis method.

In the case of the gene cloning method, the DNA can be prepared in large amounts by incorporating the product of amplifying a normal nucleic acid into a vector selected from a plasmid vector, a phage vector or the chimera vector of a plasmid and phage, and introducing it into an arbitrary host capable of multiplication selected from a prokaryon microorganism such as *Escherichia coli* or *Bacillus subtilis*, eukaryon microorganism such as yeast fungus, or animal cells.

The chemosynthesis method may be a liquid phase process such as the triester method and phosphorous acid method, or a solid phase synthetic process using an insoluble carrier. In the case of the chemosynthesis method, after preparing single-stranded DNA in large amount using an automatic synthesis machine known in the art, double-stranded DNA can be prepared by performing annealing.

Amylose

Amylose is a polysaccharide having a helical structure wherein molecules of D-glucose, which is a component of starch, a homopolysaccharide for storage in higher plants, are connected by α-1,4 bonds to form a straight chain.

The molecular weight of amylose is preferably of the order of from several thousands to about 150,000 in terms of number average molecular weight.

The amylose may be a commercial product, or may be suitably prepared according to a known method.

Part of the amylose may also contain amylopectin.

The length of the rod-shaped organic molecule is not particularly limited, and can be suitably selected according to the purpose.

The diameter of the rod-shaped organic molecule is not particularly limited and may be suitably selected according to the purpose, but in the case of the α-helix polypeptide, it is of the order of 0.8 nm to 2.0 nm.

The rod-shaped organic molecule may be completely lipophilic (hydrophobic), hydrophilic, or amphiphilic wherein part is lipophilic (hydrophobic) or hydrophilic, and the other part has the opposite affinity to this part.

The wavelength of the interference light due to the optical interference unit may or may not be in the visible light region. The former case is preferred as the wavelength of the interference light can be detected visually, and it is more preferred that the wavelength of the interference light be in the visible light region after wavelength change. In this case, this interference light can be observed as an interference color, the principle whereby this interference color is observed being based on so-called structural color formation.

Structural Color Formation

Reflection of the incident light as the colored interference light is a color formation (color of interference light) in which, when an external stimulus, such as an electric field, a magnetic field, heat, light (e.g., natural light, infrared light, ultraviolet light), or the like, is applied to the film, light of a specific wavelength is reflected in accordance with the thickness of the film and the refractive index thereof, on the basis of the multilayer thin-film interference theory which is the basic principle of color formation of the scaly powder of the wings of a Morpho butterfly. As a result, color formation (colored interference light) occurs at the surface of the film. In the structural color formation, a dye or pigment is unnecessary.

Hereinafter, the principles of structural color formation will be explained.

Figure 3:
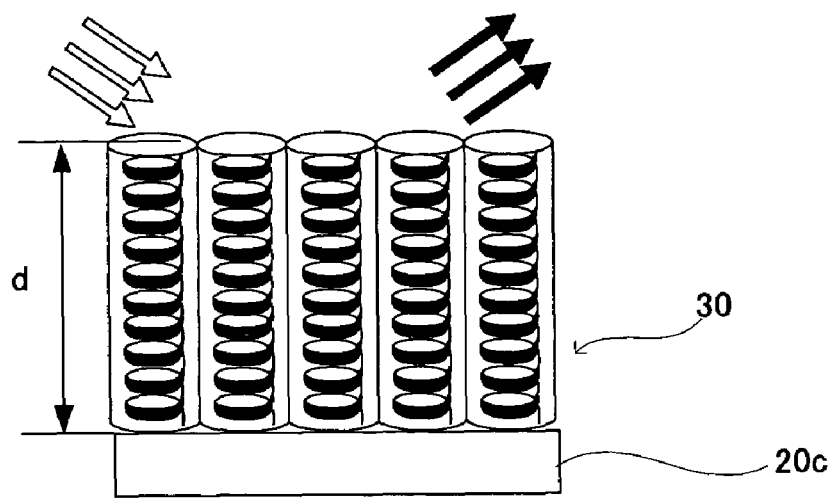
FIG. 3 is a schematic diagram illustrating structural color formation (occurrence of an interference color) by a monomolecular film (film-like material) of rod-shaped organic molecules (rod-shaped materials) provided on an optical interference substrate.
Figure 4:
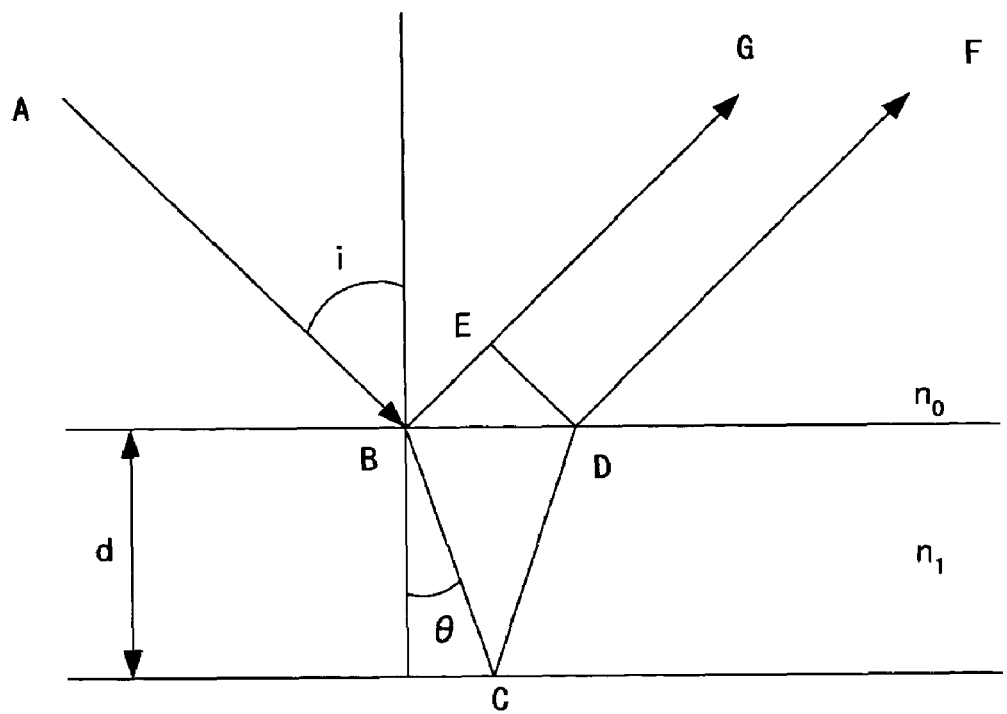
FIG. 4 is a schematic diagram for explaining the principles of structural color formation.

As shown in FIGS. 3 and 4, when the film-like material (or film-like material formed of the rod-shaped material 30 and different refractive index film in the optical interference substrate 20c) is irradiated by the optical irradiation unit, the wavelength (λ) of the interference light due to this film-like material (or film-like material formed of the rod-shaped material 30 and different refractive index film in the optical interference substrate 20c) is emphasized under the conditions shown in the following formula (2), and enfeebled under the conditions shown in the following formula (3).

$$\lambda = \frac{2tl}{m}\sqrt{n^2 - \sin^2\alpha} \qquad (2)$$

$$\lambda = \frac{4tl}{2m-1}\sqrt{n^2 - \sin^2\alpha} \qquad (3)$$

In the formula (2) and formula (3), "λ" is the wavelength (nm) of interference light, "α" is the incidence angle (°) of light on the film-like material (or film-like material formed of the rod-shaped organic molecules 30 and different refractive index film in the optical interference substrate 20c), "t" is the thickness (nm) of the film-like material (or film-like material formed of the rod-shaped organic molecules 30 and different refractive index film in the optical interference substrate 20c), "l" is the number of the film-like materials (or film-like material formed of the rod-shaped organic molecules 30 and different refractive index film in the optical interference substrate 20c), "n" is the refractive index of the film-like material (or film-like material formed of the rod-shaped organic molecules 30 and different refractive index film in the optical interference substrate 20c), and "m" is an integer of 1 or more.

The thickness of the film-like material (or film-like material formed of the rod-shaped organic molecules 30 and different refractive index film in the optical interference substrate 20c) is not particularly limited and may be suitably determined according to the purpose, but it is preferably 810 nm or less, and more preferably from 10 nm to 810 nm.

By suitably changing the thickness, the color (wavelength) of the structural color can be changed.

The film-like material may be a monomolecular film of the rod material, a laminated film of this monomolecular film, a self-assembled film, a graft polymer film, or the like.

The process for forming the film-like material is not particularly limited and an appropriate film-forming process known in the art may be used. Examples include coating, Langmuir-Blodgett method (LB method), self-assembly, graft copolymerization, and the like. In the case where the film-like material is formed by Langmuir-Blodgett method (LB method), an LB film-forming apparatus known in the art (e.g., NL-LB400 NK-MWC, Japan Laser & Electronics Laboratories) can be used.

Figure 5:
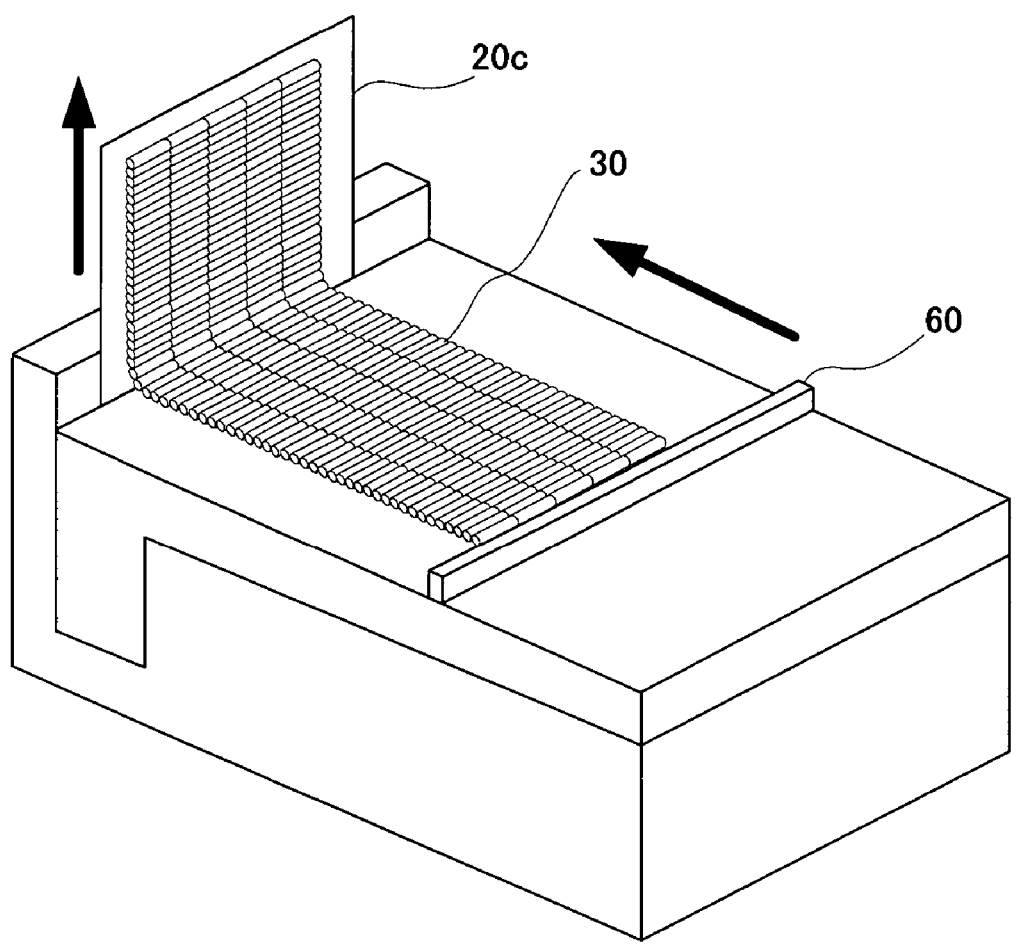
FIG. 5 is a schematic descriptive diagram showing one example of the formation of a monomolecular film (film-like material) by rod-shaped organic molecules (LB method).

The monomolecular film-like material can be formed on the optical interference substrate 20c using an extrusion member 60, for example in the state where lipophilic (hydrophobic) or amphiphilic rod-shaped organic molecules are floating on a water surface (aqueous phase), or the state where hydrophilic or amphiphilic rod-shaped organic molecules are floating on an oil surface (oil phase), i.e., a state wherein the rod-shaped organic molecules 30 are oriented as shown in FIG. 5. By repeating this operation, a laminated film comprising a desired number of monomolecular films can be formed on the optical interference substrate 20c.

At this time, it is preferred to give the surface of the optical interference substrate 20c a surface treatment for the purpose of making the rod-shaped organic molecules 30 adhere or bond, for example if the rod-shaped organic molecule 30 (e.g., an α-helix polypeptide) is hydrophilic, it is preferred to first perform a surface treatment beforehand, such as hydrophilization treatment using octadecyl trimethylsiloxane or the like.

Figure 6:
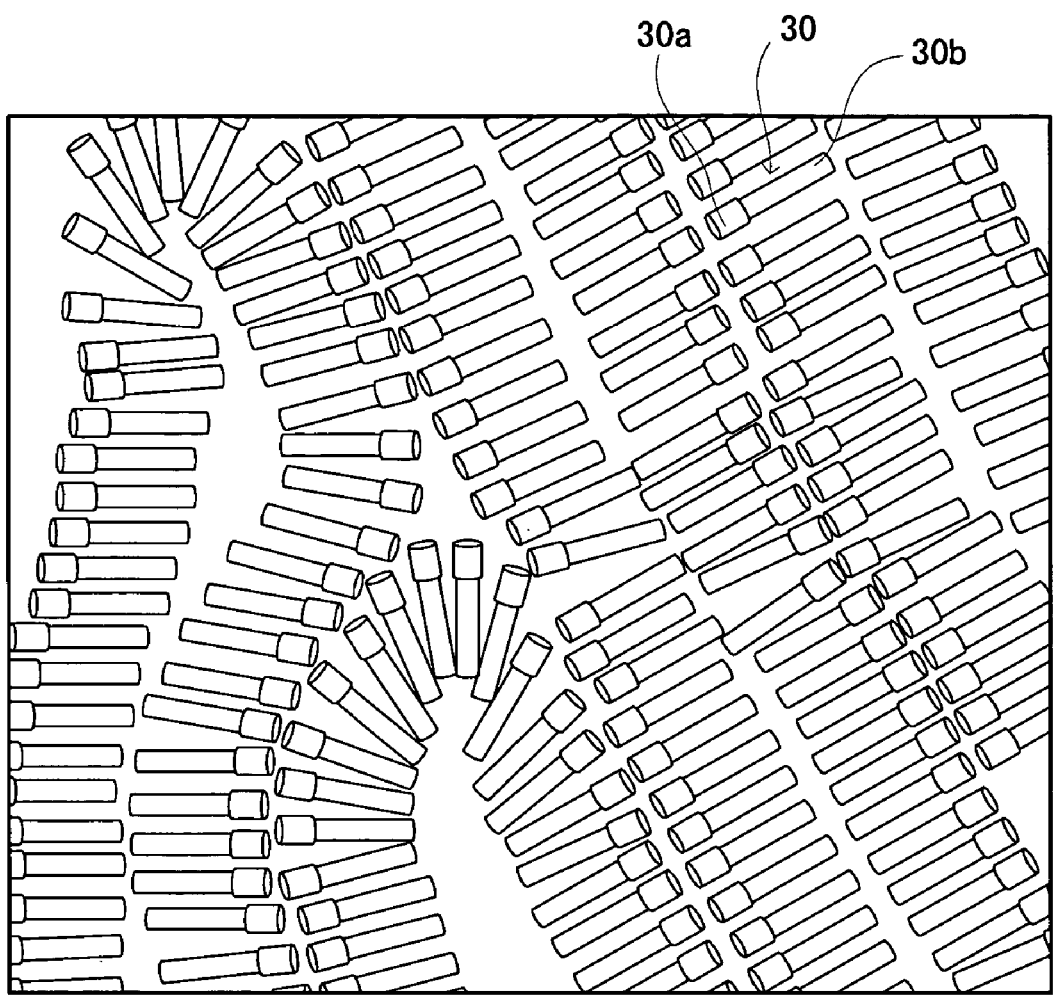
FIG. 6 is a schematic descriptive diagram showing an example of how amphiphilic rod-shaped organic molecules are oriented on water (or an aqueous phase).

When the monomolecular film of amphiphilic rod-shaped organic molecules 30 is formed, the state wherein the rod-shaped organic molecules 30 float on the oil phase or aqueous phase is such that the lipophilic parts (hydrophobic parts) 30a are oriented adjacent to each other, and the hydrophilic parts 30b are oriented adjacent to each other in the rod-shaped organic molecules 30 on the aqueous phase or oil phase, as shown in FIG. 6.

Figure 7A:
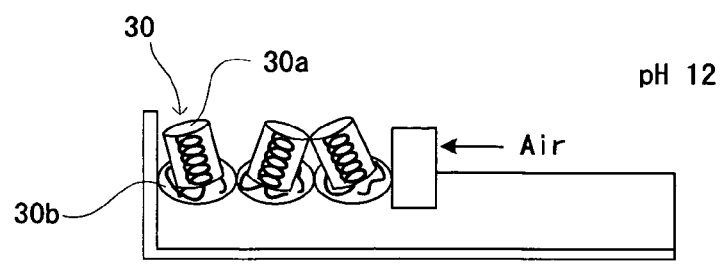
FIGS. 7A and 7B are schematic descriptive diagrams showing an example of a method for standing amphiphilic rod-shaped organic molecules on water (or an aqueous phase).
Figure 7B:
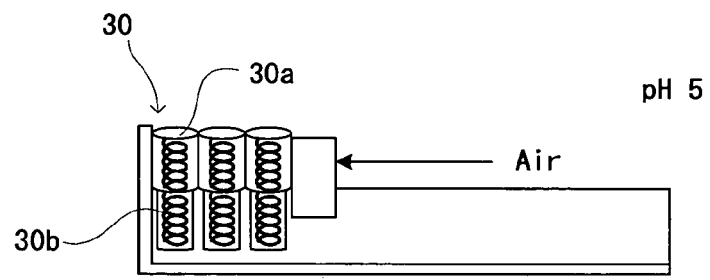

Described above is an example of a monomolecular film wherein the rod-shaped organic molecules are oriented in the plane direction of the monomolecular film (laid horizontally) or a laminated film comprising monomolecular films. A monomolecular film wherein the rod-shaped organic molecules are oriented in the thickness direction of the monomolecular film (standing state) can be formed for example as described below. Specifically, as shown in FIGS. 7A and B, first, the pH of the water (aqueous phase) is adjusted to an alkalinity of about 12 with the amphiphilic rod-shaped organic molecules 30 (α-helix polypeptide) floating on the water surface (aqueous phase). As a result, the hydrophilic parts 30b of the rod-shaped organic molecules 30 (α-helix polypeptide) lose the α-helix structure and take up a random configuration. At this time, the lipophilic parts (hydrophobic parts) 30a of the rod-shaped organic molecules 30 (α-helix polypeptide) retain their α-helix structure. Next, the pH of the water (aqueous phase) is adjusted to an acidity of about 5. As a result, the hydrophilic parts 30b of the rod-shaped organic molecules 30 (α-helix polypeptide) again take up an α-helix structure. At this time, a pressure member brought into contact with the rod-shaped organic molecules 30 (α-helix polypeptide) presses the rod-shaped organic molecules 30 (α-helix polypeptide) by air pressure from the side in the direction indicated by the arrows, and the rod-shaped organic molecules 30 remain standing on the water (aqueous phase) and the hydrophilic parts 30b become oriented effectively perpendicular to the water surface in the aqueous phase to take up an α-helix structure. Hence, as described above referring to FIG. 5, a monomolecular film can be formed on an optical interference substrate 20c by extruding on the optical interference substrate 20c using a pressure member 60 with the rod-shaped organic molecules 30 (α-helix polypeptide) aligned in an orderly manner. By repeating this operation, a laminated film comprising a desired number of monomolecular films can be formed on the optical interference substrate 20c.

The method of bonding the target acceptor to the rod-shaped organic molecules (rod-shaped object) is not particularly limited and can be suitably selected according to the type of target acceptor and rod-shaped organic molecules. Examples include the method of using covalent bonds such as ester bonds or amide bonds; the method wherein avidin is bonded to a protein, which is then bonded to a biotin-modified capturing acceptor; the method wherein a protein is labeled with streptavidin, and bonded to a biotin-modified capturing structure; and the like.

In the target detection apparatus according to the present invention, due to the use of these methods, any desired target acceptor can easily be bonded to the rod-shaped organic molecules, so unlike the case where this target acceptor is directly bonded to the substrate, the target acceptor or target can be freely selected over a wide range, the target detection apparatus can be used for a wide range of applications regardless of the detection purpose or type of target, and as the surface of the target acceptor can be kept smooth, wavelength variation unevenness of the interference light and measurement errors are small, so detection can be performed with high sensitivity.

Examples of using covalent bonds are the peptide method, diazo method, alkylation, cyanogen bromide activation, bonding by crosslinking agent, the fixing method using the Ugi reaction, the fixing method using a thiol disulfide exchange reaction, the Schiff base-forming method, the chelate bond method, the tosyl chloride method and biochemical-specific bonding, but to obtain more stable bonds such as covalent bonds, methods using the reaction of a thiol group with a maleimide group, the reaction of a pyridyl disulfide group with a thiol group and the reaction of an amino group with an aldehyde group are preferred, and the method of using a chemical binder or crosslinking agent is more preferred.

Examples of such chemical binders and crosslinking agents are carbodiimides, isocyanates, diazo compounds, benzoquinones, aldehydes, periodic acids, maleimido compounds and pyrydyl disulfide compounds. Specific examples thereof are glutaraldehyde, hexamethylene diisocyanate, hexamethylene diisothiocyanate, N,N'-polymethylene bis-iodine acetamide, N,N'-ethylene bis-maleimide, ethylene glycol bis-succinimidyl succinate, bis-diazobenzidine, 1-ethyl-3-(3-dimethyl amino propyl) carbodiimide, succinimidyl 3-(2-pyridyldithio)propionate (SPDP), N-succinimidyl 4-(N-maleimido methyl)cyclohexane-1-carboxylate (SMCC), N-sulfosuccinimidyl 4-(N-maleimido methyl)cyclohexane-1-carboxylate, N-succinimidyl (4-iodine acetyl) aminobenzoate, N-succinimidyl 4-(1-maleimidophenyl) butyrate, iminothioran, S-acetyl mercaptosuccinic acid anhydride, methyl-3-(4'-dithiopyrydyl)propionimidate, methyl-4-mercaptobutylylimidate, methyl-3-mercapto propionimidate and N-succinimidyl-S-acetyl mercaptoacetate.

In this case, the target acceptor is not directly bonded to the optical interference substrate, but the target acceptor is bonded to the rod-shaped material, and the rod-shaped material is bonded to the optical interference substrate, so for example if the target acceptor is an organic substance, instead of bonding this directly to the optical interference substrate which is an inorganic substance, it is easier to arrange it on the optical interference substrate via a bond with the rod-shaped material which is also an organic substance, and the target acceptor is also thereby stabilized. Further, even if the optical interference substrate surface is not smooth, the target acceptor can be laid flat, so the light-receiving surface irradiated by the optical irradiation unit can be smoothed, and measurement errors in the wavelength change of the interference light due to the fact that the light-receiving surface is not smooth, can be reduced.

Target Acceptor and Target Capturing Body

The target acceptor and target capturing body are not particularly limited provided that they can capture a target, and may be suitably selected according to the purpose. Examples include enzymes, coenzymes, enzyme substrates, enzyme inhibitors, host compounds, metals, antibodies, antigens, microorganisms, parasites, bacteria, viruses, virus particles, cells, cell fragments, metabolites, nucleic acids, hormones, hormone receptors, lectins, sugars, physiologically active material, physiologically active material receptors, avidin, biotin, allergens, proteins, blood proteins, tissue proteins, nucleic substances, neurotransmitters, hapten, drugs, environmental materials, chemical substances, derivatives thereof, and the like. The target acceptor and target capturing body may be the same or different.

The state of capturing is not particularly limited and can be suitably selected according to the purpose, e.g., physical adsorption or chemical adsorption. These may for example be realized by hydrogen bonds, intermolecular forces (van der Waals force), coordination bonds, ionic bonds or covalent bonds.

When the target acceptor or target capturing body is an enzyme, the target is for example a coenzyme of this enzyme; when it is a coenzyme, the target is for example an enzyme for which this coenzyme functions as a coenzyme; when it is a host compound, the target is for example a guest compound (included component) of this host compound; when it is an antibody, the target is for example a protein which is an antigen to this antibody; when it is a protein, the target is for example an antibody to which this protein is an antigen; when it is a nucleic acid, the target is for example a complementary nucleic acid to this nucleic acid, tubulin, chitin, or the like; when it is a hormone receptor, it is for example a hormone received by this hormone receptor; when it is a lectin, it is for example a sugar received by this lectin; and when it is a physiologically active material-receiving compound, it is for example a physiologically active material received by this physiologically active material-receptor.

The sample containing the target is not particularly limited and may be suitably selected according to the purpose. Examples include pathogens such as bacteria and viruses, blood, saliva, tissue pathology sections and excreta such as feces and urine. When performing a prenatal diagnosis, the sample may be embryo cells in the amniotic fluid or some dividing egg cells in a test-tube. In these samples, cell destructive treatment may be performed, directly or after concentrating as sediment by centrifuging if necessary, using one or a combination of for example enzyme treatment, heat treatment, surfactant treatment and ultrasonic treatment.

The host compound is not particularly limited provided that it has molecular recognition ability (host-guest bonding ability), and may be suitably selected according to the purpose, examples being those with a cylindrical (one-dimensional) hollow, those with a stratified (two-dimensional) hollow, or those with a cage-shaped (three-dimensional) hollow.

Examples of the host compounds comprising a cylindrical (one-dimensional) hollow are urea, thiourea, deoxycholic acid, dinitrodiphenyl, dioxytriphenylmethane, triphenylmethane, methyl naphthalene, spirochroman, PHTP (perhydrotriphenylene), cellulose, amylose and cyclodextrin (in solution, the hollows are cage-shaped).

Examples of targets which can be captured by urea are n-paraffin derivatives.

Examples of targets which can be captured by thiourea are branched and cyclic hydrocarbons.

Examples of targets which can be captured by deoxycholic acid are paraffins, fatty acids and aromatic compounds.

Examples of targets which can be captured by dinitrodiphenyl are diphenyl derivatives.

Examples of targets which can be captured by dioxytriphenylmethane are paraffin, n-alkene and squalene.

Examples of targets which can be captured by triphenylmethane are paraffins.

Examples of targets which can be captured by methylnaphthalene are n-paraffins and branched paraffins up to $C_{16}$.

Examples of targets which can be captured by spirochroman are paraffins.

Examples of targets which can be captured by PHTP (perhydrotriphenylene) are chloroform, benzene and various polymer substances.

Examples of targets which can be captured by cellulose are $H_2O$, paraffins, $CCl_4$, dyes and iodine.

Examples of targets which can be captured by amylose are fatty acids and iodine.

Cyclodextrin is a cyclic dextrin generated by decomposition of the amylase in starch, three types, $\alpha$-cyclodextrin, $\beta$-cyclodextrin and $\gamma$-cyclodextrin being known. In the present invention, cyclodextrin also includes cyclodextrin derivatives wherein some of these hydroxyl groups are replaced by other functional groups, for example, alkyl groups, allyl groups, alkoxy groups, amide groups and sulfonic acid groups.

Examples of targets which can be captured by cyclodextrin are phenol derivatives such as thymol, eugenol, resorcinol, ethylene glycol monophenyl ether and 2-hydroxy-4-methoxy-benzophenone, benzoic acid derivatives such as salicylic acid, methyl parahydroxybenzoate and ethyl p-hydroxybenzoate, and esters thereof, steroids such as cholesterol, vitamins such as ascorbic acid, retinol and tocopherol, hydrocarbons such as limonene, allyl isothiocyanate, sorbic acid, iodine molecules, methyl orange, Congo Red and 2-p-toluidinylnaphthalene-6-sulfonic acid potassium salt (TNS).

The stratified (two-dimensional) host compound may for example be a clay mineral, graphite, smectite, montmorillonite or zeolite.

Examples of targets which can be captured by clay minerals are hydrophilic substances and polar compounds.

Examples of targets which can be captured by graphite are O, $HSO_4^-$, halogens, halides and alkali metals.

Examples of targets which can be captured by montmorillonite are brucine, codeine, o-phenylenediamine, benzidine, piperidine, adenine, guanine and ribosides thereof.

Examples of targets which can be captured by zeolite are $H_2O$ or the like.

The cage-shaped (three-dimensional) host compound may for example be a hydroquinone, gaseous hydrate, tri-o-thymotide, oxyflavane, dicyanoamine nickel, cryptand, calixarene or a crown compound.

Examples of targets which can be captured by hydroquinone are HCl, $SO_2$, acetylene and rare gas elements.

Examples of targets which can be captured by gaseous hydrates are halogens, rare gas elements and lower hydrocarbons.

Examples of targets which can be captured by tri-o-thymotide are cyclohexane, benzene and chloroform.

Examples of targets which can be captured by oxyflavane are organic bases.

Examples of targets which can be captured by dicyanoamine nickel are benzene and phenol.

Examples of targets which can be captured by cryptand are $NH_4^+$ and various metal ions.

Calixarene is a cyclic oligomer wherein phenol units are linked by methylene groups, which can be synthesized under suitable conditions from phenol and formaldehyde, and whereof 4 to 8 nuclides are known. Among these, examples of targets which can be captured by p-t-butylcalixarene (n=4) are chloroform, benzene and toluene. Examples of targets which can be captured by p-t-butyl calixarene (n=5) are isopropyl alcohol and acetone. Examples of targets which can be captured by p-t-butyl calixarene (n=6) are chloroform and methanol. An example of targets which can be captured by p-t-butyl calixarene (n=7) is chloroform.

Crown compounds include not only crown ethers having oxygen as an electron-donative donor atom, but also, as an analog, large ring compounds having donor atoms such as nitrogen and sulfur as component atoms of the ring system, and also include complex cyclic crown compounds having two or more rings such as cryptand, for example, cyclohexyl-12-crown-4, dibenzo-14-crown-4, t-butylbenzo-15-crown-5, dibenzo-18-crown-6, dicyclohexyl-18-crown-6, 18-crown-6, tribenzo-18-crown-6, tetrabenzo-24-crown-8 and dibenzo-26-crown-6.

Examples of targets which can be captured by the crown compound are various metal ions such as alkaline earth metals, e.g., alkali metals such as Li, Na, K, Mg and Ca, $NH_4^+$, alkylammonium ions, guanidium ions and aromatic diazonium ions, this crown compound forming a complex therewith. Examples of other targets which can be captured by this crown compound are polar organic compounds containing C—H (acetonitrile, malonitrile and adiponitrile) having a relatively large acidity, N—H (aniline, aminobenzoic acid, amides and sulfamide derivatives) or O—H units (phenol, acetic acid derivatives), this crown compound forming a complex therewith.

The size (diameter) of the hollow of the host compound is not particularly limited and can be suitably selected according to the purpose, but from the viewpoint of manifesting a stable molecular recognition ability (host-guest bonding ability), it is preferably 0.1 nm to 2.0 nm.

Host compounds may also be classified as, for example, monomolecular host compounds, polymolecular host compounds, polymer host compounds and inorganic host compounds.

Examples of monomolecular host compounds are cyclodextrin, crown compounds, cyclophane, azacyclophane, calixarene, cyclotriveratrylene, spherand, cavitand and oligopeptides.

Examples of polymolecular host compounds are urea, thiourea, deoxycholic acid, perhydrotriphenylene and tri-o-thymotide.

Examples of polymer host compounds are cellulose, starch, chitin, chitosan and polyvinyl alcohol.

Examples of inorganic host compounds are intercalation compounds, zeolite and Hofmann type complexes.

The antibody is not particularly limited provided that it undergoes an antigen-antibody reaction with a specific antigen. Examples include polyclonal antibodies and monoclonal antibodies, and further include IgG; IgM; IgE; Fab', Fab, and F(ab')$_2$ of IgG; and the like.

The antigen is not particularly limited and can be suitably selected according to the type of antibody, for example plasma proteins, tumor markers, apoproteins, virus antigens, autoantibodies, coagulation/fibrinolysis factor, hormones, drugs in blood, and HLA antigens.

Examples of plasma proteins are immunoglobulin (IgG, IgA, IgM, IgD, IgE), complementary components (C3, C4, C5, C1q), CRP, $\alpha_1$-antitrypsin, $\alpha_1$-microglobulin, $\beta_2$-microglobulin, haptoglobin, transferrin, ceruloplasmin and ferritin.

Examples of tumor markers are α-fetoprotein (AFP), carcinoembryonic antigen (CEA), CA 19-9, CA125 and CA 15-3, SCC antigen, prostate gland acid phosphatase (PAP), PIVKA-II, γ-seminoprotein, TPA, Elastase I, nerve specific enolase (NSE) and immunosuppression acidic protein (IAP).

Examples of apoproteins are apo A-I, apo A-II, apo B, apo C-II, apo C-III and apo E.

Examples of virus antigens are hepatitis B virus (HBV)-related antigen, hepatitis C virus (HVC)-related antigen, HTLV-I, HIV, rabies virus, influenza virus and rubella virus.

Examples of HCV-related antigens are HCVc100-3 recombinant antigen, pHCV-31 recombinant antigen and pHCV-34 recombinant antigen, and mixtures thereof may be used. Examples of HIV-related antigens are virus surface antigen, e.g., HIV-I env.gp41 recombinant antigen, HIV-I env.gp120 recombinant antigen, HIV-I gag.p24 recombinant antigen and HIV-II env.p36 recombinant antigen.

Other infections apart from viruses are MRSA, ASO, toxoplasma, mycoplasma and STD.

Examples of autoantibodies are anti-microzome antibody, anti-siloglobulin antibody, antinuclear antibody, rheumatism factor, anti-mitochondrion antibody and myelin antibody.

Examples of coagulation/fibrinolysis factor are fibrinogen, fibrin cleavage product (FDP), plasminogen, $\alpha_2$-plasmin inhibitor, Antithrombin III, β-thromboglobulin, Factor VIII, Protein C and Protein S.

Examples of hormones are pituitary hormones (LH, FSH, GH, ACTH, TSH, prolactin), thyroid hormones ($T_3$, $T_4$, siloglobulin), calcitonin, parathyroid hormone (PTH), adenocoriticotropic hormones (aldosterone, cortisol), gonad hormone (hCG, estrogen, testosterone, hPL), pancreatic and gastrointestinal hormones (insulin, C-peptide, glucagon, gastrin), others (renin, Angiotensin I and II, enkephalin and erythropoietin), and the like.

Examples of drugs in blood are antiepileptics such as carbamazepine, primidone and valproic acid, circulatory organ disease drugs such as digoxin, quinidine, digitoxin and theophylline, and antibiotics such as gentamycin, kanamycin and streptomycin.

These proteins may preferably be low molecular weight molecules (about 6000 to 13000) which show high affinity with heavy metals, in particular zinc, cadmium, copper and mercury. The proteins are present in the liver, kidney and other organs of the animal, and have recently been shown to be present also in microorganisms. They have a high cysteine content, and show an amino acid distribution containing almost no aromatic residues. They are important substances which have detoxication functions, such as eliminating cadmium and mercury from the body, and also participate in the storage and distribution of trace metals indispensable to the living body such as zinc and copper.

Examples of heavy metals are alkyl mercury compounds (R—Hg), mercury or its compounds (Hg), cadmium or its compounds (Cd), lead or its compounds (Pb), hexavalent chromium ($Cr_{6^+}$), copper or its compounds (Cu), zinc or its compounds (Zn), cyan, arsenic, selenium, manganese, nickel, iron, zinc, selenium, and tin.

The optical interference unit is not particularly limited provided that it can radiate interference light, and the interference light may be radiated as transmitted light or as reflected light. In the former case, the target detection apparatus can be made a transmitting type apparatus, whereas in the latter case, the target detection apparatus can be made a reflecting type apparatus.

Wavelength Change Detecting Unit

The wavelength change detecting unit is provided in the path of the interference light and has a function to detect wavelength change using ripples or the main wavelength in a graph of transmittance against wavelength of the interference light which is irradiated from the optical interference unit.

The wavelength change detecting unit is not particularly limited provided that it has such function and may be suitably selected according to the purpose. Preferable examples include, (1) one that only allows light having a specific wavelength to pass through and that can detect this light having the specific wavelength; and (2) one that measures a spectrum before wavelength change of the interference light and a spectrum after wavelength change of the interference light so as to determine and measure the differential spectrum of the two spectra.

Among these, in the case of the (1), it is possible to detect easily, quickly, and with high sensitivity by prohibiting transmittance of interference light before the target interaction part of the optical interference unit (target detection substrate), target, and wavelength changer interact and form a complex, but by allowing transmittance of interference light having a specific wavelength after the target interaction part of the optical interference unit (target detection substrate), target, and wavelength changer interact and form a complex, changing the wavelength of the interference light to the specific wavelength. Alternatively, by allowing transmittance of interference light having specific wavelength before the target interaction part of the optical interference unit (target detection substrate), target, and wavelength changer interact and form a complex, but by prohibiting transmittance of interference light after the target interaction part of the optical interference unit (target detection substrate), target, and wavelength changer interact and form a complex, changing the wavelength of the interference light. In this way, even if it is very difficult to detect a slight change, i.e., if there is only a slight wavelength change (wavelength shift) by simply measuring the ordinary spectral curve, or even if no peak of main wavelength is formed in the graph of transmittance of the interference light, this can be easily and reliably detected. As the wavelength change detection unit detects the transmission of this interference light, the wavelength change of the interference light can be detected, and the interaction of the target with the optical interference unit, i.e., the presence of this target in the sample, can be detected easily, rapidly and with high sensitivity.

Further, from the magnitude of the transmitted light (transmitted light intensity), quantitative measurement of the target can be performed. Specifically, a calibration curve is first drawn showing the relation between the transmitted light amount of the interference light (transmitted light intensity) and the target capture amount due to the optical interference unit (target detection substrate). Hence, when the target content is measured for the sample containing the target, if the transmitted light amount of the interference light (transmitted light intensity) is measured, the target amount captured by the optical interference unit (target detection substrate) can be quantitatively measured from this calibration curve.

Alternatively, in the case of the (2), the spectral difference before and after the wavelength of the interference light has changed, i.e., the differential spectrum, is measured by the wavelength change detecting unit, so even if the change is so slight that it is very difficult to measure by measuring only the ordinary spectral curve, i.e., when there is only a very small wavelength change (wavelength shift), or even if no peak of main wavelength is formed in the graph of transmittance of the interference light, this can be detected with ease and reliability, the wavelength change can be transformed into a spectral intensity, and this can be amplified as desired. As a result, even if the wavelength change is very small of no peak of main wavelength is formed in the graph of transmittance of the interference light, it can be detected as an amplified spectral intensity, and can be detected with high sensitivity by a simple, rapid and highly sensitive detection.

Further, by measuring the spectral intensity, a quantitative measurement of the target can be performed. Specifically, a calibration curve is first drawn showing the relation between the transmitted light amount of the interference light (transmitted light intensity) and the wavelength intensity in the differential spectrum of the wavelength change (peak shift) of the interference light due to the optical interference unit (target detection substrate), or, a calibration curve is first drawn showing the relation between the wavelength intensity of the differential spectrum and the target amount captured by the optical interference unit (detection target substrate), and when the target content is measured for a sample containing the target, by measuring the wavelength intensity of the differential spectrum of the wavelength change (peak shift) of the interference light, the target amount captured by the interference unit (target detection substrate) can be quantitatively measured from this calibration curve.

A specific example of (1) is a combination of an interference filter with an optical detection sensor which can detect transmitted light which has passed through the interference filter. In this case, it is possible to detect easily, quickly, and with high sensitivity by prohibiting transmittance of interference light through the interference filter before the target interaction part of the optical interference unit (target detection substrate), target, and wavelength changer interact and form a complex, but by allowing transmittance of interference light having a specific wavelength after the target interaction part of the optical interference unit (target detection substrate), target, and wavelength changer interact and form a complex, changing the wavelength of the interference light to the specific wavelength. Alternatively, by allowing transmittance of interference light having specific wavelength before the target interaction part of the optical interference unit (target detection substrate), target, and wavelength changer interact and form a complex, but by prohibiting transmittance of interference light after the target interaction part of the optical interference unit (target detection substrate), target, and wavelength changer interact and form a complex, changing the wavelength of the interference light. In this way, even if it is very difficult to detect a slight change, i.e., even if there is only a slight wavelength change (wavelength shift) by simply measuring the ordinary spectral curve, or even if no peak of main wavelength is formed in the graph of transmittance of the interference light, this can be easily and reliably detected. When the optical detection sensor detects the interference light transmitted through the interference filter, the wavelength change of the interference light is thereby detected, and the formation of a complex through the interaction of the target interaction part of the optical interference unit (target detection substrate), target, and wavelength changer, i.e., the presence of this target in the sample is detected. As a result, even if there is only a very slight wavelength change, or even if no peak of main wavelength is formed in the graph of transmittance of the interference light, the optical detection sensor can detect the transmitted interference light, and with high sensitivity. Also, whether the interference filter transmits interference light of a specific wavelength after the target interaction part of the optical interference unit (target detection substrate), target, and wavelength changer interact and form a complex, or whether it transmits interference light of a specific wavelength before the target interaction part of the optical interference unit (target detection substrate), target, and wavelength changer interact and form a complex, if the optical detection sensor measures the transmission amount of interference light, a quantitative measurement of the target can be performed.

The interference filter is not particularly limited and may be suitably selected according to the purpose, and commercial products may also be used.

The interference filter interferes only with incident light of a specific wavelength, and transmits incident light of wavelengths other than the specific wavelength.

The optical detection sensor is not particularly limited and may be suitably selected according to the purpose, examples being a CdS cell, photodiode, photoelectric tube, pyroelectric sensor, CCD sensor or PSD sensor.

Specific examples of (2) are spectrophotometers known in the art.

In the target detection apparatus according to the present invention, the optical irradiation unit irradiates light. The optical interference unit interferes with the light irradiated from the optical irradiation unit, and radiates it as an interference light. The optical interference unit can interact with the target and change the wavelength of the interference light after the target interaction part of the optical interference unit (target detection substrate), target, and wavelength changer interact and form the complex. The wavelength change detecting unit detects the wavelength change of the interference light radiated by the optical interference unit. In this way, it is possible to detect wavelength change using the ripples without the use of an interference filter for the optical interference unit, and therefore it is possible to provide target detection apparatuses which can be produced efficiently at low cost. The target detection apparatus of the present invention can be used in various fields, and can detect various targets such as pathogens, biological substances and toxic substances with efficiency, reliability and ease. Further, these measurements may be performed quantitatively, and can be conveniently used as a diagnostic apparatus, analysis apparatus or quantitative measurement apparatus.

Use of Target Detection Apparatus

Hereinafter, the use of the target detection apparatus according to the present invention will be described. Since the process for detecting a target according to the present invention can be suitably performed using the target detection apparatus, the process is described through describing the use of the target detection apparatus.

The process for detecting a target according to the present invention includes the steps of irradiating light and detecting wavelength change.

Below, an example of the use of the target detection apparatus according to the present invention will be described with reference to FIG. 1. The optical irradiation unit irradiates light to the optical interference unit (target detection substrate). Target interaction parts (target acceptors) 20*a* of the optical interference unit (target detection substrate) 20, targets 1, and wavelength changers 10 (target capturing bodies 10*a*) interact and form complexes on the optical interference substrate. The interaction may be, for example, one in which target 1 and target interaction part (target acceptor) 20a interact first, and then target 1 and wavelength changer 10 (target capturing body 10a) interact; one in which target 1 and wavelength changer 10 (target capturing body 10a) interact first, and then target 1 and target interaction part (target acceptor) 20a interact; or one in which target interaction part (target acceptor) 20a, target 1, and wavelength changer 10 (target capturing body 10a) interact at the same time.

Accordingly, the complex is not formed when the target is not present, but when the target exists, the complex is formed, and the refractive index changes with respect to the formation of the complex. As a result, the wavelength of interference light of the light irradiated from the optical irradiation unit changes (wavelength shift) with respect to the formation of the complex.

When light is irradiated to the optical interference unit (target detection substrate), the optical interference unit can radiate light by reflection or transmission.

Hereinafter, an example of the use of the target detection apparatus according to the present invention will be further described with reference to FIG. 2. The optical interference unit (target detection substrate) has a film-like material 50 on an optical interference substrate 20c, and the film-like material 50 contains rod-shaped organic molecules 30 and target acceptor (biotin) 20b. The optical irradiation unit irradiates light to the optical interference unit (target detection substrate). Target acceptors (biotin) 20b, targets (avidin) 2, and wavelength changers (not shown) interact and form complexes on the optical interference substrate 20. The interaction may be, for example, one in which target (avidin) 2 and target acceptor (biotin) 20b interact first, and then target (avidin) 2 and wavelength changer interact; one in which target (avidin) 2 and wavelength changer interact first, and then target (avidin) 2 and target acceptor (biotin) 20b interact; or one in which target acceptor (biotin) 20b, target (avidin) 2, and wavelength changer interact at the same time.

Accordingly, the complex is not formed when the target is not present, but when the target exists, the complex is formed, and the refractive index changes with respect to the formation of the complex. As a result, the wavelength of interference light of the light irradiated from the optical irradiation unit changes (wavelength shift) with respect to the formation of the complex.

When light is irradiated to the optical interference unit (target detection substrate), the optical interference unit can radiate light by reflection or transmission.

Wavelength Changer

The wavelength changer is not particularly limited provided that it can interact with the target, and may be suitably selected according to the purpose, but it is preferred that it can interact with the target by at least one of physical adsorption and chemical adsorption. More preferably, the wavelength changer is a combination of the target capturing body which can capture the target and a wavelength changing material.

The optical properties of the wavelength changing material is not particularly limited and may be suitably selected according to the purpose. For example, it is preferred that the absolute value of the difference between the refractive index (n) of the different refractive index film and the magnitude of the complex refractive index of the wavelength changing material is 0.5 or more, where the refractive index (n) is represented in the formula for calculating the complex refractive index of the different refractive index film: complex refractive index $=n-ik$ (where "n" is refractive index, "k" is extinction coefficient, and "i" is imaginary number), and the magnitude of the complex refractive index is represented by the formula: magnitude of complex refractive index $=(n^2+k^2)^{0.5}$ (where "n" is refractive index and "k" is extinction coefficient).

When the absolute value is less than 0.5, the change may be indistinguishable from the case where the wavelength changer is not present, and therefore it is not preferable. The wavelength changing material is not particularly limited provided that it has a refractive index which is different from that of the different refractive index film of the target detection substrate. Preferable examples include metal compounds, metal nanoparticles, and the like. The metal compound may for example be a metal complex, chelate compound, or the like.

The metal compound is not particularly limited. Preferable examples include alkanethiol gold represented by the formula (1) below, benzenethiol gold represented by the formula (2) below, phenol gold represented by the formula (3) below, alkanedithiocarbonate gold represented by the formula (4) below, triazole gold represented by the formula (5) below, dialkyldithiocarbamic acid gold represented by the formula (6) below, aromatic carboxylic acid gold and aliphatic carboxylic acid gold represented by the formulae (7) and (8) below, metal complexes and chelate compounds represented by the formulae (9) to (31) below, and the like. These may be substituted by one or more substituents.

The metal compounds represented by the formulae (1) to (31) have at least one anionic part or cationic part shown in the formulae (1) to (31), and may have two or more. Moreover, the cationic part may be associated with an anionic part of the target or the target capturing body serving as a counteranion (counterion) of the cationic part, and in such case, the target or the target capturing body preferably has an anionic part represented by the following formulae (1) to (31).

Examples of the metal compound include triphenylphosphine dialkyldithiocarbamic acid gold, triethylphosphine-3-mercaptobenzoxazole gold, triphenylallicine trimethylsilyl alcohol gold, and the like.

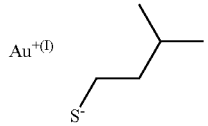

Formula (1)

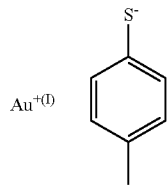

Formula (2)

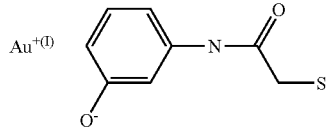

Formula (3)

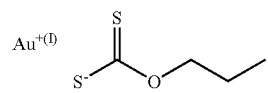

Formula (4)

-continued

Formula (5): Au⁺⁽ᴵ⁾ with 1,2,4-triazole (N-(III))

Formula (6): Au⁺⁽ᴵ⁾ with dipropyldithiocarbamate (N(propyl)₂–C(=S)–S⁻)

Formula (7): Au⁺⁽ᴵ⁾ with 2-(carboxymethylthio-acetamido)benzoate

Formula (8): Au⁺⁽ᴵ⁾ with 4-(mercaptoacetamido)phenylacetate

Formula (9): Cu²⁺⁽ᴵᴵ⁾ with pyridine-2,6-dicarboxylate

Formula (10): Cl⁻, Cu²⁺⁽ᴵᴵ⁾ with α-phenyl-2-benzimidazolemethanolate

Formula (11): Br⁻, Cu²⁺⁽ᴵᴵ⁾ with 1-methyl-2-(1-hydroxyethyl)benzimidazolate

Formula (12): Cu⁺⁽ᴵ⁾ with acetate

Formula (13): Cu⁺⁽ᴵ⁾ with acetate

Formula (14): Cu⁺⁽ᴵ⁾ with O-butyl dithiocarbonate (xanthate)

Formula (15): Cu⁺⁽ᴵ⁾ with S-[1,3-bis(methoxy)propan-2-yl] dithiocarbonate

Formula (16): Cu⁺⁽ᴵ⁾ with S–C≡N (thiocyanate)

Formula (17): Cu⁺⁽ᴵ⁾ with triisopropyl phosphite

Formula (18): Cu⁺⁽ᴵ⁾ with acetate

Formula (19): Cu⁺⁽ᴵ⁾ with imidazolidine-2-thione

Formula (20): Cu⁺⁽ᴵ⁾ with diethyldithiocarbamate

Formula (21): Cu⁺⁽ᴵ⁾ with imidazole (N-(III))

Formula (22): Zn²⁺⁽ᴵᴵ⁾ with imidazole (N-(III))

Formula (23): Zn²⁺⁽ᴵᴵ⁾ with 2-mercaptobenzothiazolate

Formula (24): Zn²⁺⁽ᴵᴵ⁾ with 1-mercaptophenazine

Formula (25): Zn²⁺⁽ᴵᴵ⁾ with 2-(imidazol-2-ylcarbonyl)benzoate

Formula (26): Ni²⁺⁽ᴵᴵ⁾ with pyridine-2,6-dicarboxylate

Formula (27): Ni²⁺⁽ᴵᴵ⁾ with picolinate (pyridine-2-carboxylate)

-continued

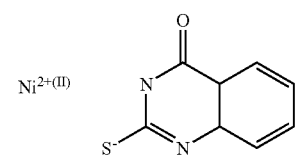

Formula (28)

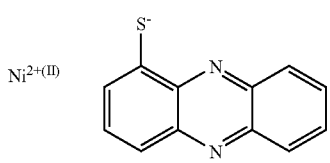

Formula (29)

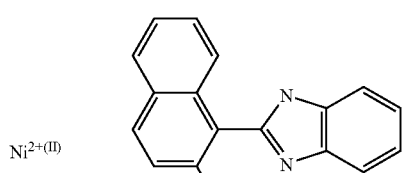

Formula (30)

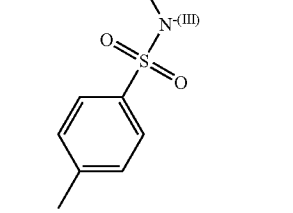

Formula (31)

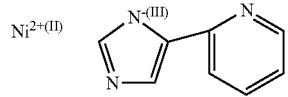

The metal nanoparticles are not particularly limited and may be suitably selected from among metal nanoparticles known in the art. Examples include gold particles, platinum particles, palladium particles, zinc particles, silver particles, nickel particles, and the like.

The optical properties of the wavelength changing material are not particularly limited and may be suitably selected according to the purpose, but it is preferable that its light absorbance exhibits wavelength dependency.

Figure 8:
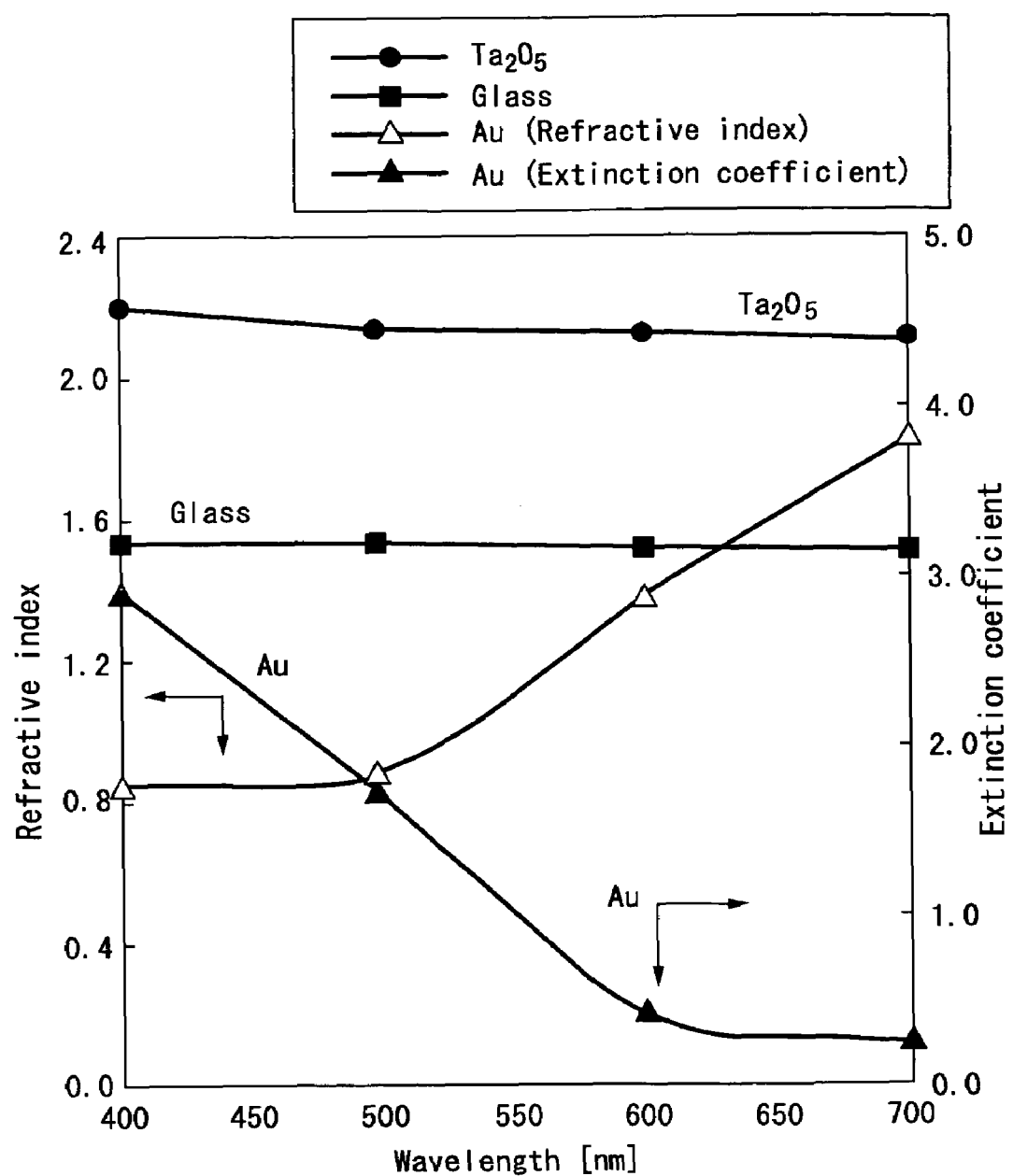
FIG. 8 is a graph illustrating wavelength dependency of light absorbance of gold.

As an example of a substance having wavelength dependency, the wavelength dependency of gold particles will be described with reference to FIG. 8. Since gold particles have high extinction coefficients (the right-hand vertical axis in FIG. 8) in the lower wavelength range as shown by the curve represented by filled triangles in FIG. 8, they absorb light irradiated from the optical irradiation unit in the lower wavelength range, particularly from 400 nm to 500 nm, to thereby yield interference light having wavelength dependency. The left-hand vertical axis of FIG. 8 represents refractive index.

By using such substance as the wavelength changing material, the light irradiated from the optical irradiation unit is specifically absorbed in the specific wavelength range. Therefore, for example by measuring the differential spectrum, the detection of wavelength change of light interfered by the optical interference unit will be simple, and will accordingly be advantageous in that it is possible to detect wavelength change (wavelength shift) with ease and certainty without using high-cost and low-productivity interference filters, that is, a peak as the main wavelength does not need to be formed in the graph of transmittance against wavelength.

The process for depositing the wavelength changing material on the target capturing body is not particularly limited. An appropriate process known in the art may be used for the deposition, and it is suitably selected according to the kind of the wavelength changing material and the target capturing body. Examples include a process which uses covalent bonds such as ester bond and amide bond, a process in which the wavelength changing material is bonded to avidin and then bonded to the target capturing body which is biotinated, and the like.

Hereinbefore described is the step of irradiating light of the process for detecting a target according to the present invention. The light irradiating step is a step in which light is irradiated to the target detection substrate; a target interaction part of the target detection substrate, a target, and a wavelength changer interact; and the irradiated light is radiated as interference light.

The detection of wavelength change of the interference light is described above as the illustration of the wavelength change detection unit of the target detection apparatus. For example, it is possible to detect easily, quickly, and with high sensitivity by prohibiting transmittance of interference light before the target interaction part of the optical interference unit (target detection substrate), target, and wavelength changer interact and form a complex, but by allowing transmittance of interference light having a specific wavelength after the target interaction part of the optical interference unit (target detection substrate), target, and wavelength changer interact and form a complex, changing the wavelength of the interference light to the specific wavelength. Alternatively, by allowing transmittance of interference light having specific wavelength before the target interaction part of the optical interference unit (target detection substrate), target, and wavelength changer interact and form a complex, but by prohibiting transmittance of interference light after the target interaction part of the optical interference unit (target detection substrate), target, and wavelength changer interact and form a complex, changing the wavelength of the interference light. In this way, even if it is very difficult to detect a slight change, i.e., if there is only a slight wavelength change (wavelength shift) by simply measuring the ordinary spectral curve, or even if no peak of main wavelength is formed in the graph of transmittance of the interference light, this can be easily and reliably detected. As the wavelength change detection unit detects the transmission of this interference light, the wavelength change of the interference light can be detected, and the formation of a complex through the interaction of the target interaction part of the optical interference unit (target detection substrate), the target, and the wavelength changer, i.e., the presence of this target in the sample, can be detected easily, rapidly and with high sensitivity.

Further, from the magnitude of the transmitted light (transmitted light intensity), quantitative measurement of the target can be performed. Specifically, a calibration curve is first drawn showing the relation between the transmitted light amount of the interference light (transmitted light intensity) and the target capture amount due to the optical interference unit (target detection substrate). Hence, when the target content is measured for the sample containing the target, if the transmitted light amount of the interference light (transmitted light intensity) is measured, the target amount captured by the optical interference unit (target detection substrate) can be quantitatively measured from this calibration curve.

Alternatively, for example, by measuring the spectral difference before and after the wavelength of the interference light has changed, i.e., the differential spectrum, with the wavelength change detection unit, the detection of wavelength change (wavelength shift) is possible with ease and reliability even if the change is so slight that it is very difficult to measure by measuring only the ordinary spectral curve, i.e., when there is only a very small wavelength change (wavelength shift), or even if no peak of main wavelength is formed in the graph of transmittance of the interference light. In this case, the wavelength change can be transformed into a spectral intensity, and this can be amplified as desired. As a result, even a very small wavelength change can be detected as an amplified spectral intensity, and can be detected with high sensitivity by a simple, rapid and highly sensitive detection.

Further, by measuring the spectral intensity, a quantitative measurement of the target can be performed. Specifically, a calibration curve is first drawn showing the relation between the transmitted light amount of the interference light (transmitted light intensity) and the wavelength intensity in the differential spectrum of the wavelength change (peak shift) of the interference light due to the optical interference unit (target detection substrate), or, a calibration curve is first drawn showing the relation between the wavelength intensity of the differential spectrum and the target amount captured by the optical interference unit (detection target substrate), and when the target content is measured for a sample containing the target, by measuring the wavelength intensity of the differential spectrum of the wavelength change (peak shift) of the interference light, the target amount captured by the interference unit (target detection substrate) can be quantitatively measured from this calibration curve.

Hereinbefore described is the step of detecting wavelength change of the process for detecting a target according to the present invention. The step of detecting wavelength change is a step in which the wavelength change of the interference light is detected.

In the process for detecting a target according to the present invention, by using the target detection substrate as the optical interference unit, it is possible to radiate interference light having a sharp spectral curve, and it is advantageous in that wavelength change (wavelength shift) of the interference light can be simply, reliably and rapidly detected with high sensitivity even if there is only a very slight wavelength change and even if a peak as the main wavelength is not formed in the graph of transmittance of the interference light. Moreover, the process for detection a target according to the present invention may be used in various fields, as it permits detection of various targets such as pathogens, biological substances and toxic substances with efficiency, reliability and ease. Further, these measurements may be performed quantitatively, and it can be conveniently used as a diagnostic process, analysis process, or quantitative measurement process.

Hereafter, the present invention will be described by means of examples, but it will be understood that the invention should not be construed as being limited thereby.

EXAMPLE 1

Preparation of Optical Interference Substrate

As the substrate, a glass substrate of 50 mm×50 mm (SCHOTT DESAG AG, B270-SUPERWITE (white plate glass)) was provided. Using Ta2O5 as a target, a layer of Ta2O5 was deposited on the glass substrate by ion assisted deposition to thereby produce an optical interference substrate.

Figure 9:
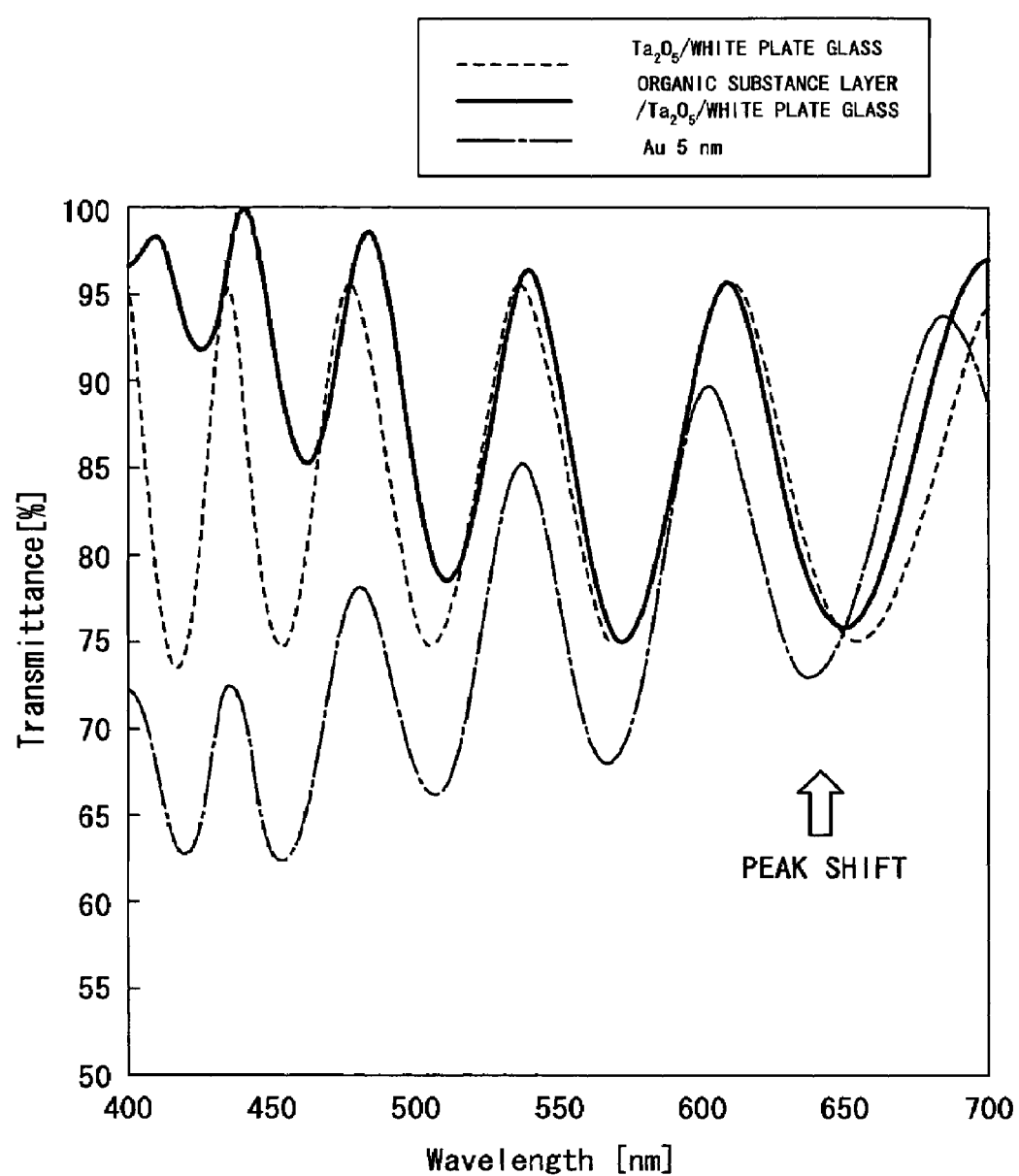
FIG. 9 is a graph showing a spectrum of interference light caused by an optical interference substrate alone; a spectrum of interference light when complexes are formed through the interaction of an optical interference unit (target detection substrate) according to the present invention, a target (avidin), and wavelength changers (supported gold nanoparticles of 5-nm diameter); and a spectrum of interference light where an organic substance layer is formed on the optical interference substrate.

Light was irradiated from the optical irradiation unit to the optical interference substrate as produced, and a sharp wavelength spectrum having ripples such as the one shown in FIG. 9 was observed. Within the wavelength spectrum, the total number of peak tops and peak bottoms in an arbitrary range of 100 nm was from 3 to 6, and the difference of transmittance between a peak top and an adjacent peak bottom was 22% or less.

The thickness (physical film thickness) and density of the $Ta_2O_5$ layer were measured, and the thickness was 1.0 μm and the density was 2.45 g/cm$^3$.

The optical interference substrate could be prepared by providing one layer of $Ta_2O_5$ on the glass substrate, and therefore the cost was low and efficiency was high.

Preparation of Target Detection Substrate

The optical interference substrate prepared as above was then immersed in a buffer solution (1.5 μM) of biotin, which serves as the target acceptor, for 0.5 hour according to a process known in the art to produce a target detection substrate in which the optical interference substrate supports biotin. The target detection substrate prepared in this manner was taken out of the biotin buffer solution and washed with pure water to remove biotin not supported by the optical interference substrate.

The preparation was such that the surface area of the target detection substrate was $1.5 \times 10^{14}$ nm$^2$ (10 mm×15 mm).

The target detection substrate was prepared using the optical interference substrate, and therefore the cost was low and efficiency was high.

Preparation of Wavelength Changer

Gold nanoparticles (diameter: 5 nm) as the wavelength changers were deposited on biotin which serves as the target capturing body, and thus wavelength changers were prepared.

The gold nanoparticles were mixed and reacted with thiolated biotin so as to be supported by the target capturing body.

Interaction Between Optical Interference Unit, Target, and Wavelength Changer

The optical interference unit, namely the target detection substrate, was immersed in an aqueous solution (1.5 μM) of avidin, which serves as the target, for 0.5 hour to allow avidin to interact with (reactively adsorb on) biotin, the target acceptor of the optical interference unit. Then, an aqueous solution containing the wavelength changer prepared as above was added dropwise to allow the target acceptor biotin of the optical interference unit, the target avidin, and the target capturing body biotin of the wavelength changer to interact (adsorb).

The cross-sectional surface area of avidin was a little less than about 30 nm$^2$ (3 nm×3 nm×3.14).

Wavelength Change Detection

As the optical irradiation unit, the light source of a spectrophotometer (Jasco Corp., V560) was used. Light (xenon lamp light) was irradiated by this optical irradiation unit so that the incidence angle on the optical interference unit was 10°.

The light-receiving unit of the spectrophotometer (Jasco Corp., V560) was positioned in the path of the reflected light (interference light) from the optical interference unit, the light originating from the optical irradiation unit, to measure the spectral wavelengths of this reflected light (interference light). As shown in FIG. 9, a sharp spectral curve having ripples was observed when only the optical interference substrate was present.

Then, biotin as the target acceptor of the optical interference unit, avidin as the target, and biotin as the target capturing body of the wavelength changer were interacted (adsorbed), after which interference light of the light irradiated from the optical irradiation unit was measured. As shown in FIG. 9, a peak shift of about 12 nm was observed for the peak bottom near 650 nm compared with the peak bottom before the formation of the complex.

Accordingly, the formation of the complex through interaction (adsorption) of biotin as the target acceptor of the optical interference unit, avidin as the target, and biotin as the target capturing body of the wavelength changer, that is, the existence of avidin as the target was detected.

In the spectral curve of the interference light, no peak as the main wavelength was formed and only the ripples were obtained. By using the gold nanoparticles as the wavelength changer, light absorption occurs, particularly in the wavelength range of from 400 nm to 500 nm as described above, and a wavelength-dependent spectral curve having ripples was observed. Accordingly, although no peak as the main wavelength was formed, it was possible to detect a peak shift with ease and certainty.

Calculation of Avidin Adsorption Amount

The number of avidin adsorptions on the target detection substrate can be calculated by dividing the surface area of the substrate by cross-sectional area of one avidin molecule, and was found to be $1.5 \times 10^{14}/3 \times 10^1 = 5 \times 10^{12}$ molecules. Next, the number of adsorbed avidin on this substrate in moles can be calculated by dividing this number of adsorptions by Avogadro's number, and was found to be $5 \times 10^{12}/6 \times 10^{23} = 8.3 \times 10^{-12}$ M=8.3 pM.

Therefore, it was found that the avidin adsorption amount for a wavelength shift in the interference light of 12 nm is 8.3 pM.

Further, when the surface area of the target detection substrate was approximately 5 mm$^2$, the wavelength shift (peak bottom shift) of the interference light for an avidin adsorption amount of 1.4 pM, was of the order of 12 nm. Converting this to a weight of avidin, and assuming that the molecular weight of avidin is approximately 68,000, we obtain $1.4 \times 10^{-12}$ M $\times 68,000 = 9.5 \times 10^{-8}$ g (95 ng), which corresponds to an adsorption amount of 7.9 ng for a peak shift (wavelength shift) of 1 nm (7.9 ng/nm).

<Detection of Wavelength Change by Differential Spectrum Measurement and Quantitative Measurement of Target>

Figure 10:
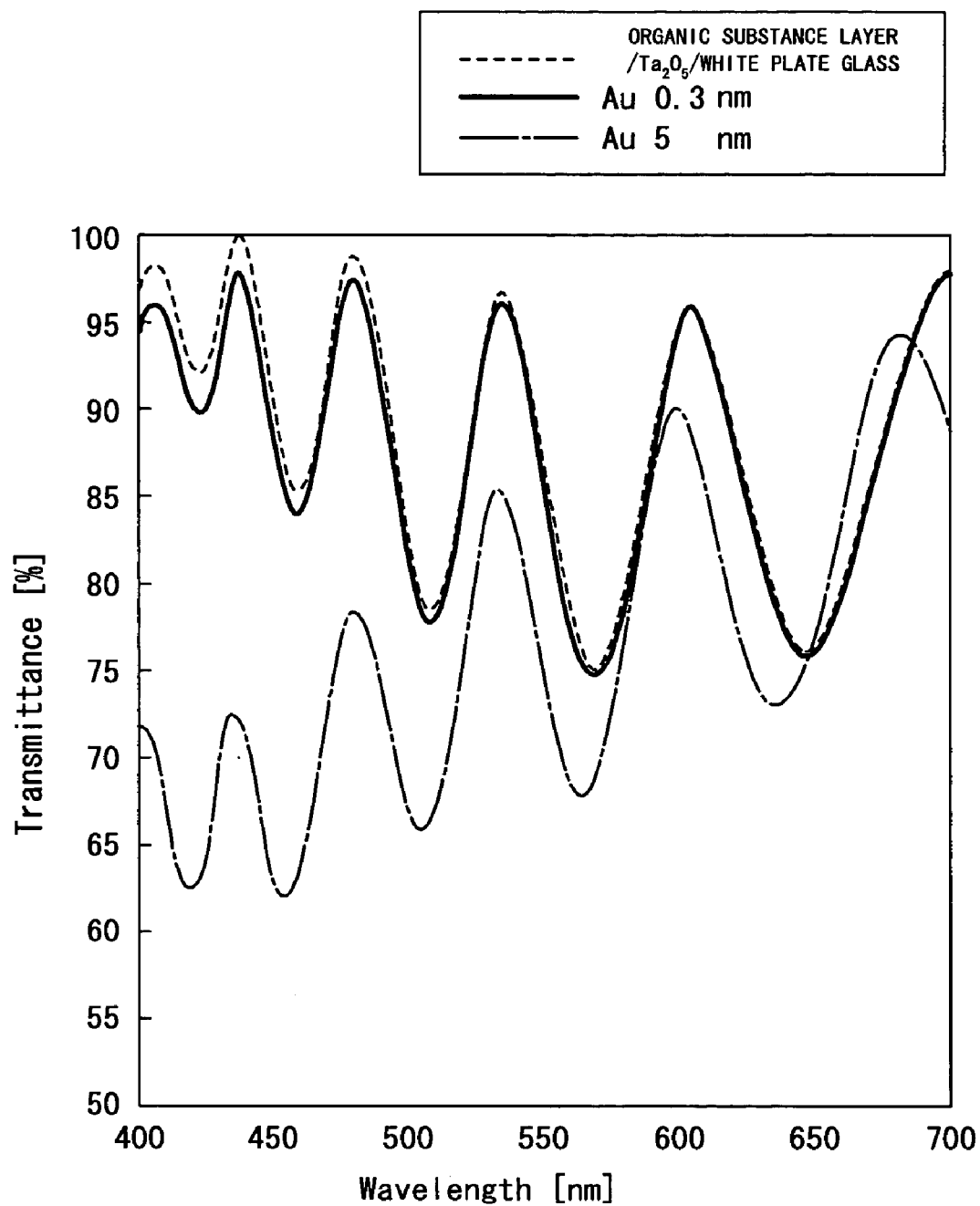
FIG. 10 is a graph showing a spectrum of interference light for each of two types of wavelength changers used where complexes are formed through the interaction of an optical interference unit (target detection substrate) according to the present invention, a target (avidin), and wavelength changers (supported gold nanoparticles); and a spectrum of interference light where an organic substance layer is formed on the optical interference substrate.
Figure 11:
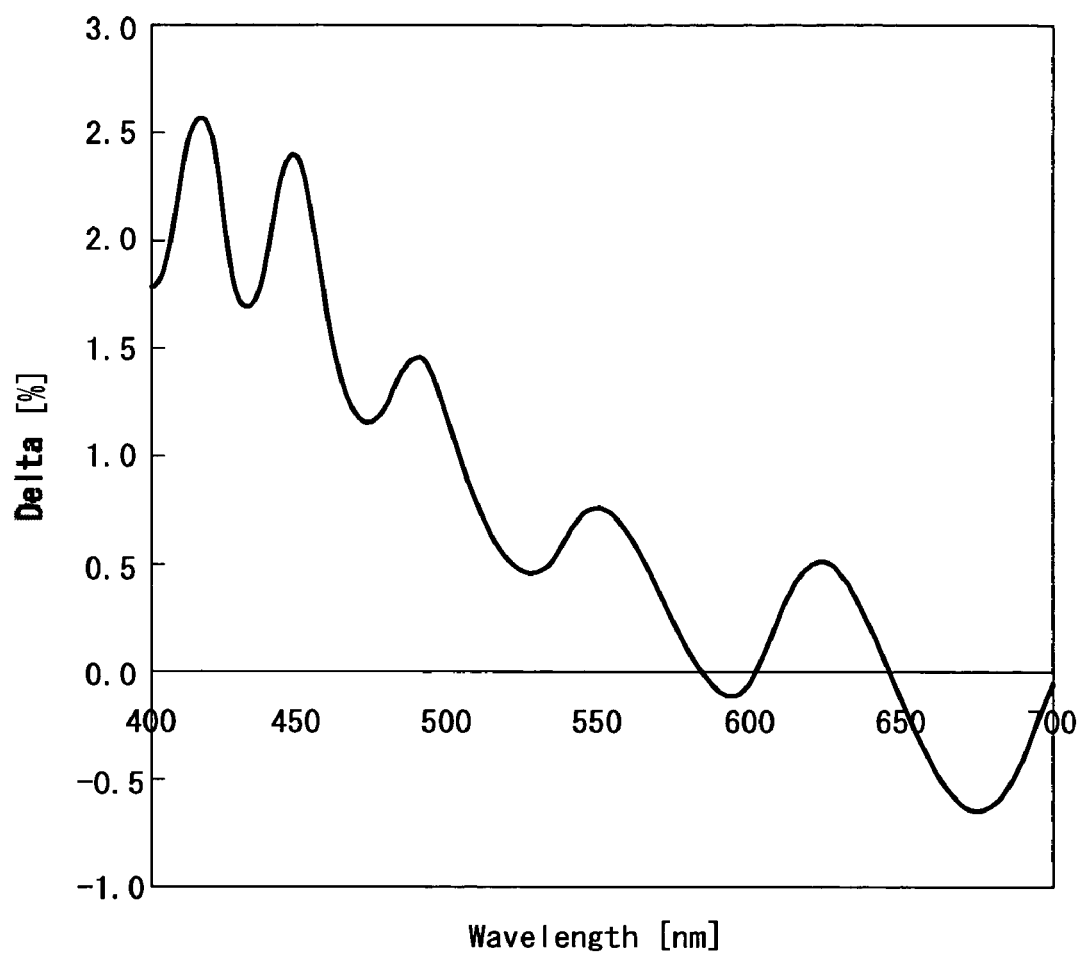
FIG. 11 is a graph showing a differential spectrum of the spectra of FIGS. 9 and 10, where one is the spectrum of interference light caused by an optical interference substrate alone, and the other is the spectrum of interference light in which gold nanoparticles of 0.3-nm diameter are used.

In some cases, after measuring a spectrum of the interference light of the optical interference substrate and a spectrum of the interference light upon formation of the complex, it may turn out to be difficult to detect wavelength shift of the interference light from the spectrum curve data because no peak as the main wavelength is formed in the spectral curves and wavelength shift is very small. Referring to FIG. 10, when the gold particles having a diameter of 5 nm were replaced with gold particles with a diameter of 0.3 nm, the spectral curve of the 0.3 nm-diameter gold particles and the spectral curve where an organic substance layer was formed on the Ta$_2$O$_5$ layer of the optical interference substrate were almost identical to each other, and therefore it was difficult to detect wavelength shift of the interference light from the spectral curve data when the 0.3 nm-diameter gold particles were used as the wavelength changing material. Here, the organic substance layer contained biotin as the target acceptor, avidin as the target, and biotin interacting with each other. However, when the differential spectrum of the two spectral data was taken by the spectrophotometer, the result was as shown in FIG. 11, and the wavelength difference of the two spectra, which was very difficult to detect in FIG. 10, could be shown as a large wavelength difference. Therefore, by detecting the differential spectrum, the wavelength difference of the interference light can be detected without measurement error, and with simplicity, rapidity and high sensitivity. This differential spectrum can be obtained as a spectral intensity, and may therefore be amplified as desired by the spectrophotometer. In other words, even if the spectral intensity is very small, it can be detected with high sensitivity by amplification.

If the procedure below is followed, by measuring the spectral intensity, a quantitative measurement of the target can be performed. Specifically, a calibration curve is first drawn showing the relation between the transmitted light amount of the interference light (transmitted light intensity) and the wavelength intensity in the differential spectrum of the wavelength change (peak shift) of the interference light due to the optical interference unit (target detection substrate), or, a calibration curve is first drawn showing the relation between the wavelength intensity of the differential spectrum and the target amount captured by the optical interference unit (detection target substrate), and when the target content is measured for a sample containing the target, by measuring the wavelength intensity of the differential spectrum of the wavelength change (peak shift) of the interference light, the target amount captured by the interference unit (target detection substrate) can be quantitatively measured from this calibration curve.

EXAMPLE 3

The spectral change (peak shift) of interference light was measured in the same manner as in Example 1 except that the gold particles as the wavelength changing material in Example 1 were replaced with alkanethiolated gold represented by the following Formula (1).

The alkanethiolated gold was mixed and reacted with thiolated biotin so as to be supported by the target capturing body.

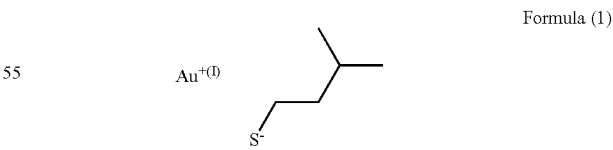

Formula (1)

As a result for the measurement, a spectral curve having ripples similar to the spectral curve of FIG. 10 where 0.3 nm-diameter gold nanoparticles were used was obtained, and at the peak bottom near 650 nm, a peak shift of about 3 nm compared with the peak bottom before the formation of the complex was observed.

Accordingly, the formation of the complex through interaction (adsorption) of biotin as the target acceptor of the optical interference unit, avidin as the target, and biotin as the target capturing body of the wavelength changer, that is, the existence of avidin as the target was detected.

In the spectral curve of the interference light, no peak as the main wavelength was formed and only the ripples were obtained. By using alkanethiolated gold represented by the above-mentioned Formula (1) as the wavelength changer, light absorption occurs, particularly in the wavelength range of from 400 nm to 500 nm as described above, and a wavelength-dependent spectral curve having ripples was observed. Accordingly, although no peak as the main wavelength was formed, it was possible to detect a peak shift with ease and certainty.

Calculation of Avidin Adsorption Amount

By the same manner of Example 1, the amount of avidin adsorption was calculated, and it was found that a peak shift (wavelength shift) of 1 nm was equivalent to 31.7 ng of adsorption (31.7 ng/nm).

The present invention can provide target detecting apparatuses and target detecting processes which can detect various targets such as pathogens, biological substances and toxic substances without using a costly measuring apparatus, which can detect these targets with a low measurement error, high efficiency, simplicity, speed and sensitivity, and which can make a quantitative detection thereof. The present invention can also provide target detection substrates and optical interference substrates which can suitably be used in such apparatuses and processes.

What is claimed is:

1. An optical interference substrate, comprising:
a substrate; and
a different refractive index film disposed on or above the substrate, the different refractive index film having a refractive index different from the refractive index of the substrate, wherein the optical interference substrate interferes with irradiated light to thereby radiate interference light, and the total number of peak tops and peak bottoms in a graph of transmittance against wavelength of the interference light is from 1 to 20 in an arbitrary wavelength range of 100 nm.

2. An optical interference substrate according to claim 1, wherein the difference between transmittance of a peak top and transmittance of an adjacent peak bottom in a graph of transmittance against wavelength of the interference light is 40% or less within a wavelength range of from 300 nm to 800 nm.

3. An optical interference substrate according to claim 1, wherein the difference between transmittance of a peak top and transmittance of an adjacent peak bottom in a graph of transmittance against wavelength of the interference light is 35% or less within a wavelength range of from 300 nm to 800 nm.

4. An optical interference substrate according to claim 1, wherein the different refractive index film comprises an oxygen-containing compound.

5. An optical interference substrate according to claim 4, wherein the oxygen-containing compound is at least one of a metal oxide and a non-metal oxide.

6. An optical interference substrate according to claim 5, wherein the metal oxide is selected from the group consisting of $Ta_2O_5$, $TiO_2$, and $SiO_2$.

7. An optical interference substrate according to claim 1, wherein the different refractive index film has a thickness of from 0.01 μm to 100 μm.

8. An optical interference substrate according to claim 1, wherein the different refractive index film has a density of from 1.0 g/cm$^3$ to 3.0 g/cm$^3$.

9. An optical interference substrate according to claim 1, wherein the substrate is formed of one selected from a semiconductor, ceramic, metal, glass, silica glass, and plastic.

10. A target detection substrate, comprising:
an optical interference substrate; and
a target interaction part disposed on or above the optical interference substrate, the target interaction part capable of interacting with a target
wherein the optical interference substrate contains:
a substrate; and
a different refractive index film disposed on or above the substrate, the different refractive index film having a different refractive index from that of the substrate,
wherein the optical interference substrate interferes with irradiated light to thereby radiate interference light, and the total number of peak tops and peak bottoms in a graph of transmittance against wavelength of the interference light is from 1 to 20 in an arbitrary wavelength range of 100 nm.

11. A target detection substrate according to claim 10, wherein the target detection substrate is capable of interfering with irradiated light to thereby radiate interference light, and the target interaction part is capable of interacting with a target, so as to enable detection of the target by detecting a wavelength change of interference light caused by interaction of the target interaction part, the target, and a wavelength changer.

12. A target detection substrate according to claim 10, wherein the interaction is at least one of physical adsorption and chemical adsorption.

13. A target detection substrate according to claim 10, wherein the target interaction part is a target acceptor capable of capturing a target.

14. A target detection substrate according to claim 11, wherein the wavelength changer comprises:
a target capturing body capable of capturing a target; and
a wavelength changing material having a refractive index different from the refractive index of the different refractive index film of the target detection substrate, wherein the wavelength changing material is capable of changing a wavelength of interference light radiated from the detection substrate.

15. A target detection substrate according to claim 14, wherein an absolute value of a difference between a refractive index "n" of the different refractive index film and a magnitude of a complex refractive index of the wavelength changing material is 0.5 or more, wherein the size of the complex refractive index is represented by the formula:

magnitude of complex refractive index=$(n^2+k^2)^{0.5}$ wherein "n" is a refractive index and "k" is a extinction coefficient.

16. A target detection substrate according to claim 14, wherein the wavelength changing material is a substance wherein light absorbance thereof exhibits wavelength dependency.

17. A target detection substrate according to claim 14, wherein the wavelength changing material is at least one of a metal compound and metal nanoparticle.

18. A target detection substrate according to claim 17, wherein the metal compound is at least one of a metal complex and chelate compound.

19. A target detection substrate according to claim 17, wherein the metal compound is at least one of alkanethiol gold, benzenethiol gold, phenol gold, alkanedithiocarbonate gold, triazole gold, dialkyldithiocarbamic acid gold, aliphatic carboxylic acid gold, aromatic carboxylic acid gold, and derivatives thereof.

20. A target detection substrate according to claim 17, wherein the metal nanoparticle is at least one selected from a gold particle, platinum particle, palladium particle, zinc particle, silver particle, and nickel particle.

21. A target detection substrate according to claim 13, wherein at least one of the target acceptor and target capturing body is selected from an enzyme, coenzyme, enzyme substrate, enzyme inhibitor, host compound, metal, antibody, antigen, microorganism, parasite, bacterium, virus, virus particle, cell, cell fragment, metabolite, nucleic acid, hormone, hormone receptor, lectin, sugar, physiologically active material, physiologically active material receptor, avidin, biotin, allergen, protein, blood protein, tissue protein, nucleic substance, neurotransmitter, hapten, drug, environmental material, chemical substance, and derivatives thereof.

22. A target detection substrate according to claim 21, wherein the host compound is selected from a monomolecular host compound, polymolecular host compound, polymer host compound and inorganic host compound,
  wherein the monomolecular host compound is selected from cyclodextrin, a crown compound, cyclophane, azacyclophane, calixarene, cyclotriveratrylene, spherand, cavitand and oligopeptide;
  the polymolecular host compound is selected from urea, thiourea, deoxycholic acid, perhydrotriphenylene and tri-o-thymotide;
  the polymer host compound is selected from cellulose, starch, chitin, chitosan and polyvinyl alcohol; and
  the inorganic host compound is selected from an intercalation compound, zeolite and Hofmann type complex.

23. A target detection substrate according to claim 13, wherein the target is avidin, and at least one of the target acceptor and the target capturing body is biotin.

24. A target detection apparatus, comprising:
  an optical irradiation unit which irradiates light;
  an optical interference unit which interacts with a target and a wavelength changer, and is capable of changing wavelength of interference light of light irradiated by the optical irradiation unit; and
  a wavelength change detection unit provided in a path of the interference light, which wavelength change detection unit is capable of detecting wavelength change of the interference light radiated from the optical interference unit,
  wherein the optical interference unit includes at least a target detection substrate including:
  an optical interference substrate; and
  a target interaction part disposed on or above the optical interference substrate, the target interaction part capable of interacting with a target
  wherein the optical interference substrate contains:
    a substrate; and
    a different refractive index film disposed on or above the substrate, the different refractive index film having a different refractive index from that of the substrate,
  wherein the optical interference substrate interferes with irradiated light to thereby radiate interference light, and the total number of peak tops and peak bottoms in a graph of transmittance against wavelength of the interference light is from 1 to 20 in an arbitrary wavelength range of 100 nm.

25. A target detection apparatus according to claim 24, wherein the optical irradiating unit is capable of irradiating a linear luminous flux.

26. A target detection apparatus according to claim 24, wherein the optical irradiating unit is a laser light irradiation device.

27. A target detection apparatus according to claim 24, wherein the wavelength change detection unit is capable of transmitting light having a specific wavelength, and of detecting transmittance of the light having a specific wavelength.

28. A target detection apparatus according to claim 24, wherein the wavelength change detection unit comprises:
  an interference filter; and
  an optical detection sensor capable of detecting light transmitted through the interference filter.

29. A target detection apparatus according to claim 24, wherein the wavelength change detection unit is capable of measuring a spectrum of interference light before a wavelength change and a spectrum of interference light after the wavelength change, and of measuring a differential spectrum of the two spectra.

30. A target detection apparatus according to claim 29, wherein the wavelength change detection unit is capable of transforming the differential spectrum into a spectral intensity, and of amplifying the spectrum intensity.

31. A target detection apparatus according to claim 29, wherein the wavelength change detection unit is a spectrophotometer.

32. A process for detecting a target, comprising:
  irradiating light to a target detection substrate, including:
    an optical interference substrate; and
    a target interaction part disposed on or above the optical interference substrate, the target interaction part capable of interacting with the target
  wherein the optical interference substrate contains:
    a substrate; and
    a different refractive index film disposed on or above the substrate, the different refractive index film having a different refractive index from that of the substrate,
  wherein the optical interference substrate interferes with irradiated light to thereby radiate interference light, and the total number of peak tops and peak bottoms in a graph of transmittance against wavelength of the interference light is from 1 to 20 in an arbitrary wavelength range of 100 nm;
  allowing the target interaction part of the target detection substrate, the target, and a wavelength changer to interact;
  radiating the irradiated light as interference light; and
  detecting a wavelength change of the interference light.

* * * * *

(12) INTER PARTES REEXAMINATION CERTIFICATE (0220th)
United States Patent
Kawano et al.

(10) Number: US 7,330,276 C1
(45) Certificate Issued: Dec. 28, 2010

(54) OPTICAL INTERFERENCE SUBSTRATE, TARGET DETECTING SUBSTRATE, TARGET DETECTING APPARATUS, AND TARGET DETECTING PROCESS

(75) Inventors: Tetsuo Kawano, Shizuoka (JP);
Tomohiro Kodama, Shizuoka (JP);
Shintaro Washizu, Shizuoka (JP);
Takatoshi Kinoshita, Aichi (JP)

(73) Assignee: Fujifilm Corporation, Minato-ku, Tokyo (JP)

Reexamination Request:
No. 95/000,392, Aug. 22, 2008

Reexamination Certificate for:
Patent No.: 7,330,276
Issued: Feb. 12, 2008
Appl. No.: 10/859,244
Filed: Jun. 3, 2004

(51) Int. Cl.
*G01B 9/02* (2006.01)

(52) U.S. Cl. .................................... 356/517
(58) Field of Classification Search ............ None
See application file for complete search history.

(56) References Cited

U.S. PATENT DOCUMENTS 6,392,756 B1    5/2002    Li et al.

*Primary Examiner*—Tuan H Nguyen

(57) ABSTRACT

Provided are target detection substrate for target detecting apparatuses capable of detecting various targets such as pathogens, biological substances and toxic substances without using a costly measuring apparatus; which can detect these targets with a low measurement error, high efficiency, simplicity, speed and sensitivity; and which can make a quantitative detection thereof. The target detection substrate includes at least a target interaction part which can interact with a target on an optical interference substrate, which optical interference substrate includes a substrate and a different refractive index film having a different refractive index from that of the substrate disposed on the substrate, and interferes irradiated light to radiate it as interference light where the total number of peak tops and peak bottoms in a graph of transmittance against wavelength of the interference light is from 1 to 20 in an arbitrary wavelength range of 100 nm.

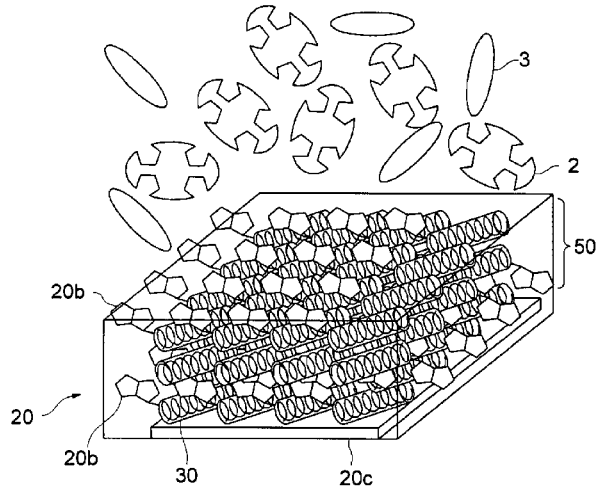

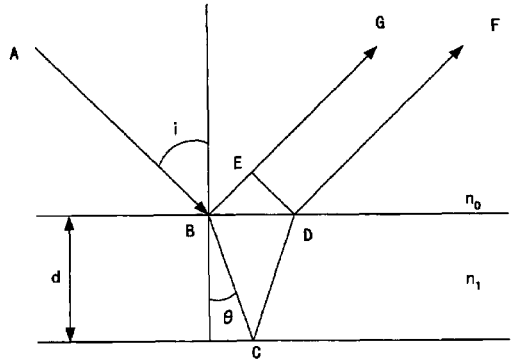

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

The patentability of claims 18-20 and 22-23 is confirmed.

Claims 1-17, 21 and 24-32 are cancelled.

\* \* \* \* \*